(12) United States Patent
Weber et al.

(10) Patent No.: US 10,647,945 B2
(45) Date of Patent: May 12, 2020

(54) USE OF A GEL-LIKE POLYMER COMPOSITION WHICH CAN BE OBTAINED BY POLYMERIZING AN ACID GROUP-CONTAINING MONOMER IN THE PRESENCE OF A POLYETHER COMPOUND IN FORMULATIONS FOR AUTOMATIC DISHWASHING

(71) Applicant: BASF SE, Ludwigshafen (DE)

(72) Inventors: Heike Weber, Mannheim (DE); Yannick Fuchs, Weinheim (DE); Helmut Witteler, Wachenheim (DE); Roland Boehn, Maxdorf (DE); Ralph Rieger, Ludwigshafen (DE)

(73) Assignee: BASF SE (DE)

( * ) Notice: Subject to any disclaimer, the term of this patent is extended or adjusted under 35 U.S.C. 154(b) by 161 days.

(21) Appl. No.: 14/902,487

(22) PCT Filed: Jul. 2, 2014

(86) PCT No.: PCT/EP2014/064083
§ 371 (c)(1),
(2) Date: Dec. 31, 2015

(87) PCT Pub. No.: WO2015/000969
PCT Pub. Date: Jan. 8, 2015

(65) Prior Publication Data
US 2016/0152928 A1 Jun. 2, 2016

(30) Foreign Application Priority Data

Jul. 3, 2013 (EP) .................................... 13174938

(51) Int. Cl.
| | | |
|---|---|---|
| C11D 3/37 | (2006.01) |
| A61K 8/81 | (2006.01) |
| A61K 47/32 | (2006.01) |
| C08F 2/24 | (2006.01) |
| C08F 2/44 | (2006.01) |
| C08F 20/06 | (2006.01) |
| C08F 120/06 | (2006.01) |
| C08F 283/06 | (2006.01) |
| C08L 33/02 | (2006.01) |
| C08L 71/02 | (2006.01) |
| C09D 4/06 | (2006.01) |
| C09D 133/02 | (2006.01) |
| C09J 133/02 | (2006.01) |
| C11D 1/722 | (2006.01) |
| C11D 3/386 | (2006.01) |
| C11D 3/395 | (2006.01) |
| C11D 11/00 | (2006.01) |
| C11D 17/00 | (2006.01) |

(52) U.S. Cl.
CPC .......... *C11D 3/3757* (2013.01); *A61K 8/8152* (2013.01); *A61K 47/32* (2013.01); *C08F 2/24* (2013.01); *C08F 2/44* (2013.01); *C08F 20/06* (2013.01); *C08F 120/06* (2013.01); *C08F 283/06* (2013.01); *C08L 33/02* (2013.01); *C08L 71/02* (2013.01); *C09D 4/06* (2013.01); *C09D 133/02* (2013.01); *C09J 133/02* (2013.01); *C11D 1/722* (2013.01); *C11D 3/3707* (2013.01); *C11D 3/386* (2013.01); *C11D 3/395* (2013.01); *C11D 11/0017* (2013.01); *C11D 11/0023* (2013.01); *C11D 17/003* (2013.01)

(58) Field of Classification Search
CPC ..... C11D 3/3757; C11D 1/722; C11D 3/3707; C11D 3/386; C11D 3/395; C11D 11/0017; C11D 11/0023; C11D 17/003; A61K 8/8152; A61K 47/32; C08F 2/24; C08F 2/44; C08F 20/06; C08F 120/06; C08F 283/06; C08L 33/02; C08L 71/02; C09D 4/06; C09D 133/02; C09J 133/02
USPC ........................................................ 510/222
See application file for complete search history.

(56) References Cited

U.S. PATENT DOCUMENTS

| | | | | |
|---|---|---|---|---|
| 4,624,803 A | * | 11/1986 | Balzer .................... | C11D 1/721 510/219 |
| 5,318,719 A | | 6/1994 | Hughes et al. | |
| 5,384,061 A | | 1/1995 | Wise | |
| 5,661,220 A | | 8/1997 | Faul et al. | |
| 5,750,483 A | * | 5/1998 | Welch .................. | C11D 3/3788 510/226 |

(Continued)

FOREIGN PATENT DOCUMENTS

| | | |
|---|---|---|
| CA | 2061174 A1 | 8/1992 |
| CA | 2818703 A1 | 5/2012 |

(Continued)

OTHER PUBLICATIONS

Bailey, F., et al., "Some Factors Affecting the Molecular Association of Poly(Ethylene Oxide) and Poly(Acrylic Acid) in Aqueous Solution", Polymer Preprints, vol. 1, No. 2, (1960), pp. 202-205.

(Continued)

*Primary Examiner* — Ling Siu Choi
*Assistant Examiner* — Ronald Grinsted
(74) *Attorney, Agent, or Firm* — Drinker Biddle & Reath LLP

(57) ABSTRACT

The invention relates to the use of a gel-like polymer composition, which is produced by means of a radical polymerization of an [alpha],[beta]-ethylenically unsaturated acid in the presence of at least one polyether component, in formulations for automatic dishwashing (ADW).

36 Claims, 2 Drawing Sheets

(56) References Cited

U.S. PATENT DOCUMENTS

| | | | |
|---|---|---|---|
| 6,974,852 B2 * | 12/2005 | Stanger | B01F 17/0057 524/800 |
| 7,754,804 B2 | 7/2010 | Mukherjee et al. | |
| 2003/0162679 A1 | 8/2003 | Rodrigues et al. | |
| 2006/0293467 A1 | 12/2006 | Yoneda et al. | |
| 2010/0065090 A1 * | 3/2010 | Tropsch | C11D 1/8255 134/34 |
| 2011/0150796 A1 | 6/2011 | Kim et al. | |

FOREIGN PATENT DOCUMENTS

| | | | | |
|---|---|---|---|---|
| CN | 1523095 | A | 8/2004 | |
| CN | 1814722 | A | 8/2006 | |
| DE | 4326772 | A1 | 2/1995 | |
| EP | 0499068 | A1 | 8/1992 | |
| EP | 0519603 | A1 | 12/1992 | |
| EP | 0639592 | A1 | 2/1995 | |
| EP | 0971997 | A1 | 1/2000 | |
| JP | H03177406 | A | 8/1991 | |
| JP | 2004331839 | A | 11/2004 | |
| JP | WO2004099274 | * | 11/2004 | C08F 282/06 |
| JP | 2009007350 | A | 1/2009 | |
| RU | 2011141205 | A | 5/2013 | |
| WO | WO-95035412 | A1 | 12/1995 | |
| WO | WO-9840452 | A1 | 9/1998 | |
| WO | WO-2004099274 | A1 | 11/2004 | |
| WO | WO-2005012378 | A1 | 2/2005 | |
| WO | WO-2008139151 | A1 | 11/2008 | |
| WO | WO-2010026178 | A2 | 3/2010 | |
| WO | WO-2010119076 | A1 | 10/2010 | |
| WO | WO-2012069440 | A1 | 5/2012 | |
| WO | WO-2012079256 | A1 | 6/2012 | |

OTHER PUBLICATIONS

Bromberg, "Novel Family of Thermogelling Materials via C-C Bonding between Poly(acrylic acid) and Poly(ethylene oxide)-b-poly(propylene oxide)-b-poly(ethylene oxide)", Journal of Physical Chemistry B, vol. 102, No. 11, (1998), pp. 1956-1963.

International Search Report for PCT/EP2014/064083 dated Jun. 24, 2015.

Li, X., et al., "The effects of polymer gel electrolyte composition on performance of quasi-solid-state dye-sensitized solar cells", Journal of Solid State Electronchemistry, vol. 15, No. 6, (2011), pp. 1271-1277.

Chinese Office Action for Chinese Application No. 201480048341.4, dated May 8, 2018.

English Translation of International Preliminary Report on Patentability from PCT/EP2014/064083 dated Jan. 7, 2016.

Russian Office Action for Russain Application No. 2016103334, dated Apr. 23, 2018.

* cited by examiner

USE OF A GEL-LIKE POLYMER COMPOSITION WHICH CAN BE OBTAINED BY POLYMERIZING AN ACID GROUP-CONTAINING MONOMER IN THE PRESENCE OF A POLYETHER COMPOUND IN FORMULATIONS FOR AUTOMATIC DISHWASHING

CROSS-REFERENCE TO RELATED APPLICATIONS

This application is a national stage application (under 35 U.S.C. § 371) of PCT/EP2014/064083, filed Jul. 2, 2014, which claims benefit of European Application No. 13174938.4, filed Jul. 3, 2013, both of which are incorporated herein by reference in their entirety.

BACKGROUND OF THE INVENTION

The present invention relates to the use of a polymer composition in gel form, which has been produced by subjecting an α,β-ethylenically unsaturated acid to a free-radical polymerization in the presence of at least one polyether component, in formulations for machine dishwashing (automatic dish washing, ADW).

STATE OF THE ART

Machine dishwashing processes in the domestic and commercial sector comprise a plurality of successive steps, the first comprising the mechanical removal of loosely adhering food residues, the second the actual cleaning operation with the aid of a machine dishwasher, and the third generally consisting of a rinsing step, which is followed by the drying of the cleaned dishware. These operations are conducted in more or less automated form, the central unit used being a machine dishwasher in which at least the cleaning step and generally also the subsequent rinsing step and/or the drying step are conducted.

In machine dishwashers for the domestic sector, the soiled dishware is generally cleaned in a single chamber, and the aforementioned treatment steps proceed successively in a controlled program. Fresh water passes through the softening unit to the pump well and is sprayed by means of moving spray arms over the ware to be rinsed. Water-insoluble substances rinsed off are filtered out in the pump well. In the second rinse cycle, a generally alkaline cleaning composition is added to the rinse water, heated to the set temperature and distributed over the ware to be rinsed. In the last rinse cycle, a rinse aid is added to the treatment liquid, which reduces the surface tension, as a result of which the treatment liquid runs more easily off the ware. After the last rinse cycle, the contents are dried. The components used in the rinse cycle, such as water treatment agents, cleaning compositions, rinse aids, etc., can be used either in the form of individual components or in multicomponent formulations. Multifunctional detergents of this kind comprise surfactants for rinsing and a polymer for water softening. In that case, it is unnecessary to separately dispense a rinse aid and a salt for water softening into the machine dishwasher.

Commercial machine dishwashers consist basically of stationary bath tanks from which an essentially aqueous cleaning solution is jetted or sprayed onto the dishware, which moves past these baths on a conveyor belt, such that the used solution flows back into the bath tanks again. Water enters the last bath tank, flows via overflows in the manner of a cascade through all the other tanks and leaves the machine via the overflow of the first tank. The application of a generally highly alkaline cleaning solution generally takes place with the aid of the nozzles provided therefor, or of a specific spraying system normally arranged in the middle region of the machine.

In formulations for machine dishwashing, polyethers or surfactants are frequently used together with polyacrylic acid, in which case polyacrylic acid assumes the role of an incrustation inhibitor or dispersant. The problem is that polyethers and surfactants are frequently of zero or only limited compatibility in liquid form with polyacrylic acid, and so mixing results in phase separation or in precipitates, which greatly restricts the possible uses of at least one of the components. More particularly, it has not been possible to date to provide transparent gel formulations comprising polyetherols or surfactants containing polyether groups in combination with polymers containing acid groups and especially with polyacrylic acid. However, the consumer prefers formulations in gel form both because of their performance properties and for esthetic reasons.

For many current applications, gel-forming or film-forming polymer compositions have to fulfill a complex profile of demands.

The literature discloses numerous processes for preparing gels from polyacrylic acids. These gels, however, are usually water-insoluble, since they are based on crosslinked polyacrylic acid. Other gels are water-soluble but are based on copolymers of acrylic acid with hydrophobic monomers and therefore have lower performance as incrustation inhibitors or dispersants than pure polyacrylic acid. Further gels are based on high molecular weight polyacrylic acid, which is likewise not advantageous for use as an incrustation inhibitor or dispersant and increases the processing problems.

EP 0 971 997 B1 describes a liquid detergent formulation comprising a nonionic surfactant and an anionic polymer. The polymer has a molecular weight of more than 100 000 g/mol. The formulation is an about 25% aqueous solution. There is no description of formulations in gel form for machine dishwashing.

EP 0 499 068 A1 describes reaction products of alkoxylates and vinylic monomers, at least some of which bear functional groups which can react with the OH groups of the alkoxylates in a condensation. The reaction products are prepared out by either polymerizing the vinylic monomers in the presence of the alkoxylates and then subjecting the product of the polymerization to a condensation, or by first polymerizing the vinylic monomers and then subjecting the product of the polymerization to a condensation with the alkoxylates. In the case that acrylic acid is used as vinylic monomer, the reaction product in each case is thus an ester of polyacrylic acid. In the working examples, the alkoxylates used are exclusively EO-PO block copolymers having a high PO content and polytetrahydrofuran. The polymers described serve as emulsion breakers for rapid dewatering of crude oils. There is no description of use in formulations in gel form for machine dishwashing.

A similar process is described in DE 4326772 A1. Toluene or xylene is additionally used here as solvent. The use of aromatic solvents is undesirable for products which are to be used in consumer goods, since the complete removal of the solvent is very time-consuming and energy-intensive. The reaction products are liquids which are described as esterified polyacrylic acids. Ester formation runs counter to the effect of the polymers, for example as an incrustation inhibitor, and is undesirable in applications where the use of very substantially pure polyacrylic acid is required. This document does not describe use of the polymers in formulations in gel form for machine dishwashing either.

X. Li et al. in Journal of Solid State Electrochemistry (2011), 15(6), 1271-1277 and J. H. Wu et al. in Advanced Materials, 2007, 19, 4006-4011, describe preparation processes for polyacrylic acid-polyethylene glycol gels for use in dye-sensitized solar cells.

WO 2008/139151 A1 describes a process in which polyethylene glycol is mixed with acrylic acid, isobornyl acrylate and further components, and cured by UV exposure to give a solid gel. On the basis of the composition, it is apparent the person skilled in the art that the gel is not water-soluble. The gels serve as an indicator that a data carrier, for example a computer-readable compact disk, has not been used before.

WO 2010/026178 A2 describes, on page 62 and in example 19, a precipitation polymerization in which acrylic acid is polymerized in the presence of a surfactant. The handling of a large amount of organic solvents based on relatively little acrylic acid and surfactant is necessary for this process. Moreover, the reaction product comprises a large amount of polymerized vinylpyrrolidone and alkyl-PEG methacrylate, which makes the reaction product unsuitable as an incrustation inhibitor. Again, there is no description of use of the gels obtained for machine dishwashing.

F. E. Bailey at al. describe, in Polymer Preprints, American Chemical Society, Division of Polymer Chemistry, 1960, vol. 1, issue 2, p. 202-205 and the literature cited therein, the formation of molecular association complexes of ethylene oxide polymers having a very high molecular weight with polymeric acids such as polyacrylic acid in aqueous solutions. Depending on the solvent used, the pH and the concentration of the polymers, the complexes are precipitated or remain in solution. The preparation of firm gels requires dissolution of the components in solvents, then mixing of these and removal of the solvent again, which is associated with additional process steps which make such a process uneconomic for practical use. There is no disclosure of use of the gels for machine dishwashing.

Lev Bromberg describes, in Journal of Physical Chemistry B (1998), 102, 11, 1956-1963, a material having thermoreversible gel formation, which is prepared by polymerizing acrylic acid in the presence of a PEO-PPO-PEO block copolymer. The reaction is effected in the absence of external solvents, in order to achieve a high proportion of branching and crosslinking in the products obtained. These are neither water-soluble nor transparent. Possible fields of use mentioned for these polymers, merely in quite general terms, are pharmacy and nutritional supplements (p. 1956, left-hand column, "Introduction").

WO 2004/099274 describes a process for preparing polymer mixtures by polymerizing monomers of the (meth)acrylic acid type in the presence of a compound having a polyalkylene glycol structure. The polymer mixtures obtained are to contain proportions of graft copolymers, the polyalkylene glycol component and the (meth)acrylic acid component remaining homogeneous in the mixture even after prolonged storage. The polymerization is necessarily effected in the presence of water having a high water content in the initial charge at the start of the reaction. The polymer mixtures obtained by the process are suitable for various detergent applications, especially for prevention of resoiling.

EP 0 639 592 A1 describes graft copolymers obtainable by polymerizing a (meth)acrylic acid-containing polymer composition in the presence of a polyether compound having more than 80 mol % of ethylene oxide units. The polymerization is effected essentially without solvent and at temperatures above 100° C. It is regarded as critical for the achievement of high grafting levels that the solvent content of the reaction mixture is never more than 5% by weight. The polymers obtained serve as builders for liquid washing compositions or, optionally after postcrosslinking, as water-absorbing resins.

WO 2005/012378 describes aqueous dispersions of water-soluble polymers of anionic monomers and the use thereof. Example 4 (page 19 lines 14-27) relates to the polymerization of acrylic acid in the presence of stabilizers, which are polypropylene glycols. The dispersions are used, inter alia, in personal care products and in washing and cleaning compositions. There is no description of use in gel form for machine dishwashing.

It is an object of the present invention to provide a polymer composition in gel form for use in formulations for machine dishwashing, avoiding the above-described disadvantages of the prior art.

It has now been found that, surprisingly, this object is achieved when a polymer composition which has been prepared by subjecting a monomer composition based on at least one $\alpha,\beta$-ethylenically unsaturated acid to a free-radical polymerization in the presence of a polyether component is used in formulations for machine dishwashing.

SUMMARY OF THE INVENTION

The invention firstly provides for the use of a polymer composition in gel form, obtainable by a process in which
a) a monomer composition M) is provided, consisting of
  A) at least one $\alpha,\beta$-ethylenically unsaturated acid, and
  B) 0% to 0.1% by weight, based on the total weight of the monomer composition M), of crosslinking monomers having two or more than two polymerizable $\alpha,\beta$-ethylenically unsaturated double bonds per molecule,
b) the monomer composition M) provided in step a) is subjected to a free-radical polymerization in the presence of at least one polyether component PE) selected from polyetherols having a number-average molecular weight of at least 200 g/mol and the mono- and di-($C_1$-$C_6$-alkyl ethers) thereof, surfactants containing polyether groups and mixtures thereof,
in formulations for machine dishwashing.

In a specific embodiment, the polyether component PE) comprises or the polyether component PE) consists of at least one polyetherol or a mono- or di-($C_1$-$C_2$-alkyl ether) thereof comprising predominantly or exclusively ethylene oxide units incorporated as alkylene oxide units.

When the polyether component PE) comprises a polyetherol having repeat propylene oxide units or a mono- or di-($C_1$-$C_6$-alkyl ether) of a polyetherol having repeat propylene oxide units, the proportion of these repeat propylene oxide units preferably averages not more than 18 units per molecule.

When the polyether component PE) comprises a polyetherol having repeat propylene oxide units or a mono- or di-($C_1$-$C_6$-alkyl ether) of a polyetherol having repeat propylene oxide units, the proportion of these repeat propylene oxide units preferably averages not more than 17 units per molecule, more preferably not more than 15 units per molecule, especially not more than 10 units per molecule.

In a further specific embodiment, the free-radical polymerization in step b) is effected in the presence of a solvent S) selected from water, $C_1$-$C_6$-alkanols, polyols other than PE), the mono- and dialkyl ethers thereof, and mixtures thereof. In a specific execution for production of transparent gels, the solvent S) is selected from 1,2-propylene glycol, the isomeric dipropylene glycols and mixtures thereof.

In a further specific embodiment, the reaction mixture during the polymerization in step b) and the polymer composition obtained in step b) are not subjected to any condensation with removal of a low molecular weight reaction product and/or in the presence of a condensation catalyst.

The invention further provides a method for machine cleaning of dishware, in which the dishware to be cleaned is contacted with a treatment solution comprising a formulation for machine dishwashing as defined above and hereinafter.

DESCRIPTION OF THE INVENTION

Figure 1:
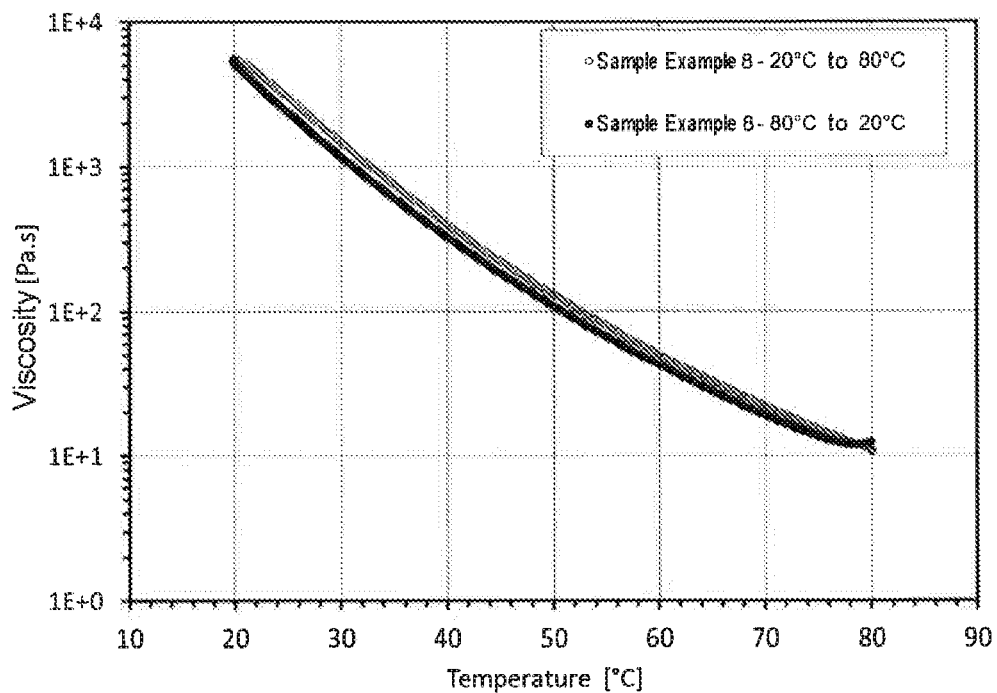
FIG. 1 shows the viscosity as a function of temperature for the gel from example 8 of table 1.

The inventive use of polymer compositions in gel form in formulations for machine dishwashing has the following advantages:

The polymer compositions used in accordance with the invention can be provided in the form of clear gels. They are suitable for formulations for machine dishwashing which, in a specific execution, are themselves in gel form.

The polymer compositions used are notable both for high compatibility between polyether component and polyacrylic acid and for high compatibility with further surfactants.

In the production of the polymer compositions used in the formulations used in accordance with the invention, it is possible to dispense substantially or completely with the use of crosslinking monomers. The polymer compositions thus obtained are advantageously water-soluble.

The inventive polymer compositions are in the form of gels under standard conditions (20° C.). "Gel-like consistency" is shown by formulations which have a higher viscosity than a liquid and which are especially self-supporting, meaning that they retain any shape imparted to them without shape-stabilizing encasement. In contrast to solid formulations, however, formulations in gel form can be deformed or converted to a fluid form easily by heating and/or with application of shear forces. The viscosity of the polymer compositions in gel form at 20° C. is preferably within a range from greater than 600 to about 10 000 000 mPa·s, more preferably from 1000 to 1 000 000 mPa·s, especially from 2000 to 500 000 mPa·s. The viscosity at 20° C. and the viscosity profile as a function of temperature for the samples to be examined were examined by means of a rotary rheometer (DHR-1 from TA Instruments with Peltier system, plate/plate geometry, Ø 40 mm, h=1 mm) at temperatures of 20° C. to 80° C. Temperature ramp ($\gamma$=1% with $M_{min}$=100 μNm). Measurement temperature(s) of 80° C. to 20° C. and back, two runs each (cooling/heating rate 2 K/min). Measurement time 30 min per run.

In the context of this application, some compounds which can be derived from acrylic acid and methacrylic acid are abbreviated by insertion of the "(meth)" syllable into the compound derived from acrylic acid.

In the context of the present invention, the expression "alkyl" encompasses straight-chain and branched alkyl groups. This preferably includes $C_1$-$C_{40}$-alkyl groups, more preferably $C_1$-$C_{30}$-alkyl groups.

Suitable short-chain alkyl groups are, for example, straight-chain or branched $C_1$-$C_6$-alkyl groups, preferably $C_1$-$C_4$-alkyl groups. Suitable longer-chain alkyl groups are, for example, straight-chain or branched $C_7$-$C_{40}$-alkyl groups, preferably $C_8$-$C_{30}$-alkyl groups. These are preferably predominantly linear alkyl radicals as also occur in natural or synthetic fatty acids and fatty alcohols, and also oxo alcohols, or predominantly linear alkenyl radicals as also occur in natural or synthetic fatty acids and fatty alcohols, and also oxo alcohols, which may be mono-, di- or polyunsaturated.

Suitable alkyl groups are especially methyl, ethyl, propyl, isopropyl, n-butyl, 2-butyl, sec-butyl, tert-butyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, arachyl, behenyl, lignoceryl, melissyl, etc.

In the context of the present invention, the expression "alkenyl" encompasses straight-chain and branched alkenyl groups. Suitable alkenyl groups may have one or more C—C double bonds. This preferably includes $C_2$-$C_{40}$-alkenyl groups, more preferably $C_4$-$C_{30}$-alkenyl groups. Suitable longer-chain $C_8$-$C_{30}$-alkenyl groups include, for example, n-octenyl, n-nonenyl, n-decenyl, n-undecenyl, n-dodecenyl, n-tridecenyl, n-tetradecenyl, n-pentadecenyl, n-hexadecenyl, n-heptadecenyl, n-octadecenyl, n-nonadecenyl, n-eicosenyl, n-docosenyl, n-tetracosenyl, hexacosenyl, triacontenyl, etc.

The inventive polymer compositions are prepared by free-radical polymerization of the monomer composition M) in the presence of at least one polyether component PE) which generally does not have any copolymerizable double bond. This affords specific polymer compositions having advantageous properties. Without being bound to a theory, this may be attributable, for example, to an effect of the polyether component PE) as a protective colloid or emulsifier. This may also result, for example, from at least partial grafting onto the polyether component as graft base. However, mechanisms other than grafting are also conceivable. The inventive polymer compositions quite generally comprise the process products of free-radical polymerization, which are understood to mean, for example, graft polymers, homo- and copolymers of the monomers present in the monomer mixture M), mixtures of graft polymers with ungrafted compounds in the polyether component PE) and any desired mixtures.

During and after the polymerization in step b), the reaction mixture and the polymer composition obtained in step b) are especially not subjected to any condensation with removal of a low molecular weight reaction product and/or in the presence of a condensation catalyst. This is understood to mean that specifically no additional measures are conducted with the aim of increasing the ester group content of the polymer composition obtained by the process according to the invention.

In a preferred execution of the first variant, the inventive polymer compositions are in the form of a transparent gel. The transparency of a material is determined by its absorption and scattering characteristics, i.e. the light transmitted and the appearance looking through the material. The total transmission (transparency) is the ratio of transmitted light to incident light. The measure used for the transparency is the transmittance τ: it is the quotient of the luminous flux $\varphi_n$ behind and $\varphi_v$ in front of the material to be tested, and is reported in percent. This value comprises, as well as the absorption, also the scattering and reflection losses. The transmittance is generally determined in air and is reported as a function of wavelength.

In the context of the invention, the transparency ($T_L$) is determined at a wavelength of 500 nm. The reference parameter used for maximum transparency ($T_L$ of 100%) is water. Preferably, the polymer composition used in accordance with the invention, in the form of a transparent gel, has a $T_L$ measured at 500 nm of at least 85%, more preferably of at least 90%, based on the transparency of water.

Monomer Composition M)

The monomer composition M) provided in step a) comprises, as component A), at least one α,β-ethylenically unsaturated acid.

The monomer composition M) provided in step a) preferably consists of
  acrylic acid as α,β-ethylenically unsaturated carboxylic acid A1),
  optionally at least one further α,β-ethylenically unsaturated acid A2), and
  0% to 0.1% by weight, based on the total weight of the monomer composition M), of crosslinking monomers having two or more than two polymerizable α,β-ethylenically unsaturated double bonds per molecule.

If the monomer composition provided in step a) comprises at least one further α,β-ethylenically unsaturated acid, it is preferably selected from carboxylic acids, sulfonic acids, phosphonic acids and mixtures thereof.

In a first preferred embodiment, component A) consists solely of acrylic acid (=monomer A1).

In a second preferred embodiment, component A) consists of acrylic acid (=monomer A1) and at least one further, different α,β-ethylenically unsaturated acid (=monomer A2).

The further α,β-ethylenically unsaturated acid A2) is preferably selected from methacrylic acid, ethacrylic acid, α-chloroacrylic acid, crotonic acid, maleic acid, itaconic acid, citraconic acid, mesaconic acid, glutaconic acid, aconitic acid, fumaric acid, 2-acrylamido-2-methylpropanesulfonic acid, vinylsulfonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, styrenesulfonic acid, vinylphosphonic acid, allylphosphonic acid and mixtures thereof.

The acid monomers A) are preferably used in protonated (i.e. non-neutralized) form for polymerization.

More preferably, the monomer composition M) consists of acrylic acid or mixtures of acrylic acid with methacrylic acid.

In a preferred embodiment, the monomer composition M) consists to an extent of at least 80% by weight, preferably to an extent of at least 90% by weight, especially to an extent of at least 95% by weight, based on the total weight of the monomers used, of acrylic acid.

More particularly, exclusively acrylic acid is used as monomer composition M).

Crosslinker B)

The inventive polymer composition consists of uncrosslinked or lightly crosslinked polymers. The monomer composition M) used for preparation of the inventive polymer composition therefore comprises only small amounts, if any, of crosslinking monomers B). Crosslinkers in the context of the invention are compounds having two or more than two polymerizable ethylenically unsaturated double bonds per molecule.

Preferably, crosslinkers B) are used in an amount of 0% to 0.1% by weight, more preferably 0% to 0.05% by weight, based on the total weight of the monomer composition M). In a specific embodiment, the monomer composition M) does not comprise any crosslinking monomers B) having two or more than two polymerizable α,β-ethylenically unsaturated double bonds per molecule.

Suitable crosslinkers B) are, for example, acrylic esters, methacrylic esters, allyl ethers or vinyl ethers of at least dihydric alcohols. The OH groups of the parent alcohols may be fully or partly etherified or esterified; however, the crosslinkers comprise at least two ethylenically unsaturated groups.

Examples of the parent alcohols are dihydric alcohols such as ethane-1,2-diol, propane-1,2-diol, propane-1,3-diol, butane-1,2-diol, butane-1,3-diol, butane-2,3-diol, butane-1,4-diol, but-2-ene-1,4-diol, pentane-1,2-diol, pentane-1,5-diol, hexane-1,2-diol, hexane-1,6-diol, decane-1,10-diol, dodecane-1,2-diol, dodecane-1,12-diol, neopentyl glycol, 3-methylpentane-1,5-diol, 2,5-dimethylhexane-1,3-diol, 2,2,4-trimethylpentane-1,3-diol, cyclohexane-1,2-diol, cyclohexane-1,4-diol, 1,4-bis(hydroxymethyl)cyclohexane, hydroxypivalic acid neopentyl glycol monoester, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetrahydrofurans each having molecular weights of 200 to 10 000. Apart from the homopolymers of ethylene oxide and propylene oxide, it is also possible to use block copolymers of ethylene oxide or propylene oxide or copolymers incorporating ethylene oxide and propylene oxide groups. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars such as sucrose, glucose, mannose. The polyhydric alcohols can of course also be used after reaction with ethylene oxide or propylene oxide, in the form of the corresponding ethoxylates and propoxylates respectively. The polyhydric alcohols can also first be converted to the corresponding glycidyl ethers by reaction with epichlorohydrin.

Further suitable crosslinkers B) are the vinyl esters or the esters of monohydric unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. It is also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers B) are esters of unsaturated carboxylic acids with the above-described polyhydric alcohols, for example oleic acid, crotonic acid, cinnamic acid or 10-undecenoic acid.

Suitable crosslinkers B) are also straight-chain or branched, linear or cyclic, aliphatic or aromatic hydrocarbons having at least two double bonds which, in the case of aliphatic hydrocarbons, must not be conjugated, e.g. divinylbenzene, divinyltoluene, octa-1,7-diene, deca-1,9-diene, 4-vinyl-1-cyclohexene, trivinylcyclohexane or polybutadienes having molecular weights of 200 to 20 000.

Also suitable as crosslinkers B) are the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids such as acrylic acid, methacrylic acid, itaconic acid, maleic acid, or at least dibasic carboxylic acids as described above.

Also suitable as crosslinkers B) are triallylamine and triallylmonoalkylammonium salts, e.g. triallylmethylammonium chloride or methylsulfate.

Also suitable are N-vinyl compounds of urea derivatives, at least difunctional amides, cyanurates or urethanes, for example of urea, ethyleneurea, propyleneurea or tartramide, e.g. N,N'-divinylethyleneurea or N,N'-divinylpropyleneurea.

Further suitable crosslinkers B) are divinyldioxane, tetraallylsilane or tetravinylsilane.

Polyether Component PE)

Suitable polyether components PE) are polyetherols having a number-average molecular weight of at least 200 g/mol and the mono- and di($C_1$-$C_6$-alkyl ethers) thereof.

Suitable polyetherols and the mono- and di($C_1$-$C_6$-alkyl ethers) thereof may be linear or branched, preferably linear. Suitable polyetherols and the mono- and di($C_1$-$C_6$-alkyl ethers) thereof generally have a number-average molecular weight in the range from about 200 to 100 000, preferably 300 to 50 000, more preferably 500 to 40 000. Suitable polyetherols are, for example, water-soluble or water-dispersible nonionic polymers having repeat alkylene oxide units. Preferably, the proportion of repeat alkylene oxide units is at least 30% by weight, based on the total weight of the compound. Suitable polyetherols are polyalkylene glycols, such as polyethylene glycols, polypropylene glycols, polytetrahydrofurans and alkylene oxide copolymers. Suitable alkylene oxides for preparation of alkylene oxide copolymers are, for example, ethylene oxide, propylene oxide, epichlorohydrin, 1,2- and 2,3-butylene oxide. Suitable examples are copolymers of ethylene oxide and propylene oxide, copolymers of ethylene oxide and butylene oxide, and copolymers of ethylene oxide, propylene oxide and at least one butylene oxide. The alkylene oxide copolymers may comprise the copolymerized alkylene oxide units in random distribution or in the form of blocks. Preferably, the proportion of repeat units derived from ethylene oxide in the ethylene oxide/propylene oxide copolymers is 40% to 99% by weight. Particularly preferred polyether components PE) are ethylene oxide homopolymers and ethylene oxide/propylene oxide copolymers.

Suitable polyether components PE) are additionally the mono- and di($C_1$-$C_2$-alkyl ethers) of the above-described polyetherols. Preference is given to polyalkylene glycol monomethyl ethers and polyalkylene glycol dimethyl ethers.

Suitable polyether components PE) are additionally surfactants containing polyether groups. In general, nonionic and ionic surfactants having at least one nonpolar group and at least one polar group and comprising a polyether group are suitable.

The surfactants containing polyether groups PE) are preferably selected from alkyl polyoxyalkylene ethers, aryl polyoxyalkylene ethers, alkylaryl polyoxyalkylene ethers, alkoxylated animal and/or vegetable fats and/or oils, fatty amine alkoxylates, fatty acid amide alkoxylates, fatty acid diethanolamide alkoxylates, polyoxyethylene sorbitan fatty acid esters, alkyl polyether sulfates, aryl polyether sulfates, alkylaryl polyether sulfates, alkyl polyether sulfonates, aryl polyether sulfonates, alkylaryl polyether sulfonates, alkyl polyether phosphates, aryl polyether phosphates, alkylaryl polyether phosphates, glyceryl ether sulfonates, glyceryl ether sulfates, monoglyceride (ether) sulfates, fatty acid amide ether sulfates, polyoxyalkylene sorbitan fatty acid esters and mixtures thereof.

The preferred nonionic surfactants include surfactants containing polyether groups PE), for example:

alkyl polyoxyalkylene ethers which derive from low molecular weight $C_3$-$C_6$ alcohols or from $C_7$-$C_{30}$ fatty alcohols. The ether component here may be derived from ethylene oxide units, propylene oxide units, 1,2-butylene oxide units, 1,4-butylene oxide units and random copolymers and block copolymers thereof. Suitable nonionic surfactants comprise, inter alia, surfactants of the general formula (VI)

$$R^{10}-O-(CH_2CH_2O)_x-(CHR^{11}CH_2O)-R^{12} \quad (VI)$$

in which $R^{10}$ is a linear or branched alkyl radical having 6 to 22 carbon atoms, $R^{11}$ and $R^{12}$ are each independently hydrogen or a linear or branched alkyl radical having 1 to 10 carbon atoms or H, where $R^{12}$ is preferably methyl, and x and y are each independently 0 to 300. Preferably, x=1 to 100 and y=0 to 30.

These especially also include fatty alcohol alkoxylates and oxo alcohol alkoxylates, such as isotridecyl alcohol polyoxyethylene ethers and oleyl alcohol polyoxyethylene ethers.

surfactants containing hydroxyl groups of the general formula (VII)

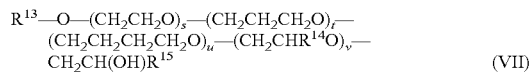

$$R^{13}-O-(CH_2CH_2O)_s-(CH_2CH_2CH_2O)_t-\\(CH_2CH_2CH_2CH_2O)_u-(CH_2CHR^{14}O)_v-\\CH_2CH(OH)R^{15} \quad (VII)$$

where the sequence of the alkylene oxide units in the compounds of the formula (VII) is arbitrary, s, t, u and v are each independently an integer from 0 to 500, where the sum of s, t, u and v is >0, $R^{13}$ and $R^{15}$ are each independently a straight-chain or branched saturated $C_1$-$C_{40}$-alkyl radical or a mono- or polyunsaturated $C_2$-$C_{40}$-alkenyl radical, and $R^{14}$ is selected from methyl, ethyl, n-propyl, isopropyl and n-butyl.

In the compounds of the general formula (VII), the sum of s, t, u and v is preferably a value of 10 to 300, more preferably of 15 to 200 and especially of 20 to 150.

Preferably, t and u are each 0. In that case, the sum of s and v is preferably a value of 10 to 300, more preferably of 15 to 200 and especially of 20 to 150.

In the compounds of the general formula (VII), $R^{13}$ and $R^{15}$ are preferably each independently a straight-chain or branched saturated $C_2$-$C_{30}$-alkyl radical. At the same time, $R^{13}$ and $R^{15}$ may also be mixtures of different alkyl radicals.

In the compounds of the general formula (VII), $R^{14}$ is preferably methyl or ethyl, especially methyl.

A preferred execution is surfactants containing hydroxyl groups of the general formula (VII.1)

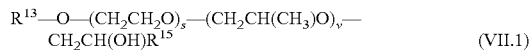

(VII.1)

where the sequence of the —($CH_2CH_2O$)— and the ($CH_2CH(CH_3)O$)— units is arbitrary, s and v are each independently an integer from 0 to 500, where the sum of s and v is >0, $R^{13}$ and $R^{15}$ are each independently a straight-chain saturated $C_1$-$C_{30}$-alkyl radical or a branched saturated $C_3$-$C_{30}$-alkyl radical or a mono- or polyunsaturated $C_2$-$C_{30}$-alkenyl radical.

In the compounds of the general formula (VII.1), the sum of s and v is preferably a value of 10 to 300, more preferably of 15 to 200 and especially of 20 to 150.

The group of these nonionic surfactants includes, for example, hydroxy mixed ethers of the general formula ($C_{6-22}$-alkyl)-CH(OH)CH$_2$O-(EO)$_{20-120}$—($C_{2-26}$-alkyl).

alcohol polyoxyalkylene esters of the general formula (VIII)

(VIII)

where the sequence of the alkylene oxide units in the compounds of the formula (VIII) is arbitrary, p and q are each independently an integer from 0 to 500, where the sum of p and q is >0, $R^{16}$ and $R^{18}$ are each independently a straight-chain or branched saturated $C_1$-$C_{40}$-alkyl radical or a mono- or polyunsaturated $C_2$-$C_{40}$-alkenyl radical, and $R^{17}$ is selected from methyl, ethyl, n-propyl, isopropyl and n-butyl.

In the compounds of the general formula (VIII), the sum of p and q is preferably a value of 10 to 300, more preferably of 15 to 200 and especially of 20 to 150.

In the compounds of the general formula (VIII), $R^{16}$ and $R^{18}$ are preferably each independently a straight-chain or branched saturated $C_4$-$C_{30}$-alkyl radical. At the same time, $R^{16}$ and $R^{18}$ may also be mixtures of different alkyl radicals.

In the compounds of the general formula (VIII), $R^{17}$ is preferably methyl or ethyl, especially methyl.

These include, for example, lauryl alcohol polyoxyethylene acetate.

alkylaryl alcohol polyoxyethylene ethers, for example octylphenol polyoxyethylene ethers, alkoxylated animal and/or vegetable fats and/or oils, for example corn oil ethoxylates, castor oil ethoxylates, tallow fat ethoxylates, alkylphenol alkoxylates, for example ethoxylated isooctyl-, octyl- or nonylphenol, tributylphenol polyoxyethylene ether, fatty amine alkoxylates, fatty acid amide and fatty acid diethanolamide alkoxylates, especially ethoxylates thereof, polyoxyalkylene sorbitan fatty acid esters.

One example of an alkyl polyether sulfate is sodium dodecyl poly(oxyethylene) sulfate (sodium lauryl ether sulfate, SLES).

Solvent S)

The free-radical polymerization in step b) can be effected in the presence of a solvent S) selected from water, $C_1$-$C_6$-alkanols, polyols other than PE), the mono- and dialkyl ethers thereof, and mixtures thereof. Suitable polyols and the mono- and dialkyl ethers thereof also comprise alkylene glycol mono($C_1$-$C_4$-alkyl) ethers, alkylene glycol di($C_1$-$C_4$-alkyl)ethers, oligoalkylene glycols having a number-average molecular weight of less than 200 g/mol and the mono($C_1$-$C_4$-alkyl) ethers and di($C_1$-$C_4$-alkyl) ethers thereof.

The solvent S) is preferably selected from water, methanol, ethanol, n-propanol, isopropanol, n-butanol, ethylene glycol, ethylene glycol mono($C_1$-$C_4$-alkyl) ethers, ethylene glycol di($C_1$-$C_4$-alkyl) ethers, 1,2-propylene glycol, 1,2-propylene glycol mono($C_1$-$C_4$-alkyl) ethers, 1,2-propylene glycol di($C_1$-$C_4$-alkyl) ethers, glycerol, polyglycerols, oligoalkylene glycols, oligoalkylene glycol mono($C_1$-$C_4$-alkyl) ethers, oligoalkylene glycol di($C_1$-$C_4$-alkyl) ethers, the last four of which have a number-average molecular weight of less than 200 g/mol, and mixtures thereof.

Suitable oligoethylene glycols are commercially available under the CTFA designations PEG-6, PEG-8, PEG-12, PEG-6-32, PEG-20, PEG-150, PEG-7M, PEG-12M and PEG-115M. These especially include the Pluriol E® products from BASF SE. Suitable alkyl polyalkylene glycols are the corresponding Pluriol A . . . E® products from BASF SE. Preference is given to the isomeric dipropylene glycols such as 1,1'-oxydi-2-propanol, 2,2'-oxydi-1-propanol, 2-(2-hydroxypropoxy)-1-propanol and mixtures thereof.

The solvent S) is more preferably selected from water, ethanol, n-propanol, isopropanol, ethylene glycol, diethylene glycol, 1,2-propylene glycol, dipropylene glycols and mixtures thereof.

In a specific embodiment, the free-radical polymerization in step b) is effected in the presence of a solvent S) comprising propylene glycol and/or dipropylene glycol.

In a further specific embodiment, the free-radical polymerization in step b) is effected in the presence of a solvent S) consisting of propylene glycol and/or dipropylene glycol and optionally water. Very specifically, the free-radical polymerization in step b) is effected in the presence of a solvent S) consisting of propylene glycol and/or dipropylene glycol.

Preferably, the polymer composition comprises the solvent S) in an amount of 0% to 50% by weight, preferably 0.1% to 40% by weight, based on the total weight of the polymer composition.

Preparation of the Polymer Compositions Used in Accordance with the Invention

The preparation of the polymer compositions used in accordance with the Invention comprises a free-radical polymerization of the monomer composition M) in the presence of at least one polyether component PE). It is preferably conducted in a feed method. This generally involves metering at least the monomers in liquid form into the reaction mixture. Monomers liquid under the metering conditions can be fed into the reaction mixture without addition of a solvent S); otherwise, the monomers are used as a solution in a suitable solvent S).

The metering rates of the monomer feed(s) and of any further feeds (initiator, chain transfer agent, etc.) are preferably chosen such that the polymerization is maintained with the desired conversion rate. The individual feeds can be added continuously, periodically, with constant or varying metering rate, and essentially simultaneously or offset in time. Preferably, all feeds are added to the reaction mixture continuously.

Preferably, the free-radical polymerization comprises, in step b) of the process according to the invention, b1) providing an initial charge comprising at least a portion of the polyether component PE), optionally at least a portion of the chain transfer agent CTA) and, if the polymerization is effected in the presence of a solvent S), optionally at least a portion of S);

b2) adding the monomer composition M) in one or more feed(s) and adding a feed comprising the free-radical initiator FRI), dissolved in a portion of at least one polyether component PE) and/or of the solvent S), and optionally adding a feed comprising the amount of the chain transfer agent CTA) which is not used in the initial charge;

b3) optionally continuing polymerization of the reaction mixture obtained in step b2).

Typically, the initial charge is heated to the polymerization temperature before adding the feeds while stirring.

Preferably, the individual reactants are added simultaneously in separate feeds, in which case the flow rates of the feeds are generally kept very substantially constant over the period of addition.

The addition of the feeds in step b2) is effected over a period which is advantageously selected such that the heat of reaction which arises in the exothermic polymerization reaction can be removed without any great technical complexity, for example without the use of a reflux condenser. Typically, the feeds are added over a period of 1 to 10 hours. Preferably, the feeds are added over a period of 2 to 8 hours, more preferably over 3 to 4 hours.

During the free-radical polymerization, the solvent optionally used and/or any condensation products formed are generally not removed. In other words, during the polymerization, there is typically only minor mass transfer with the environment within the realm of technical possibility, if any.

The polymerization can generally be effected at ambient pressure or reduced or elevated pressure. Preferably, the polymerization is performed at ambient pressure.

The polymerization is generally effected at constant temperature, but can also be varied during the polymerization if required. Preferably, the polymerization temperature is kept very substantially constant over the entire reaction period, i.e. of steps b2) and b3). According to the feedstocks which are used in the process according to the invention, the polymerization temperature varies typically within the range from 10 to 150° C. Preferably, the polymerization in step b) is effected at a temperature in the range from 20 to 150° C., preferably from 30 to 120° C., especially from 40 to 90° C. If the polymerization is not conducted under elevated pressure and at least one optional solvent S) has been added to the reaction mixture, the solvent or solvent mixture determines the maximum reaction temperature via the corresponding boiling temperatures.

The polymerization can be effected in the absence or presence of an inert gas. Inert gas is generally understood to mean a gas which, under the given reaction conditions, does not enter into any reaction with the reactants, reagents or solvents involved in the reaction, or the products formed. This includes, for example, nitrogen, argon, etc.

If the polymerization is performed in the presence of a solvent, this is selected from the above-described solvents S).

To prepare the polymers, the monomers can be polymerized with the aid of free radical-forming initiators, also referred to hereinafter as free-radical initiators or Initiators. Useful free-radical initiators (Initiators) for the free-radical polymerization in principle include all the free-radical initiators that are essentially soluble in the reaction medium as exists at the time of addition thereof and have sufficient activity at the given reaction temperatures to initiate the polymerization. It is possible to use a single free-radical initiator or a combination of at least two free-radical initiators in the process according to the invention. In the latter case, the at least two free-radical initiators can be used in a mixture or preferably separately, simultaneously or successively, for example at different times in the course of the reaction.

Free-radical initiators that can be used for the free-radical polymerization are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbamate, bis(o-tolyl) peroxide, didecanoyl peroxide, dioctanoyl peroxide, tert-butyl peroctoate, dilauroyl peroxide, tert-butyl perisobutyrate, tert-butyl peracetate, di-tert-amyl peroxide, tert-butyl hydroperoxide, 2,2'-azobisisobutyronitrile, azobis(2-amidinopropane)dihydrochloride, azobis(2,4-dimethylvaleronitrile) or 2,2'-azobis(2-methylbutyronitrile).

Also suitable are initiator mixtures or redox initiator systems, for example ascorbic acid/iron(II) sulfate/sodium peroxodisulfate, tert-butyl hydroperoxide/sodium disulfite, tert-butyl hydroperoxide/sodium hydroxymethanesulfinate, $H_2O_2/Cu^I$.

In the process according to the invention, the amount of initiator system (Initiator) used varies within the range from 0.01% to 10% by weight, preferably within the range from 0.05% to 5% by weight, more preferably within the range from 0.1% to 2% by weight.

In the process according the invention, the free-radical initiator is generally provided as a solution in a solvent comprising at least one of the aforementioned solvents S).

The amount of chain transfer agent which is typically used in the process according to the invention is 1 to 40 pphm ("parts per hundred of monomer", i.e. parts by weight based on one hundred parts by weight of monomer composition). Preferably, the amount of chain transfer agent used in the process according the invention is within the range from 1 to 30 pphm, more preferably in the range from 2 to 20 pphm.

Chain transfer agents (polymerization chain transfer agents) is the term generally used to refer to compounds with high transfer constants. Chain transfer agents accelerate chain transfer reactions and hence bring about a reduction in the polymerization level of the resulting polymers without influencing the gross reaction rate. The chain transfer agents can be divided into mono-, bi- and polyfunctional chain transfer agents, according to the number of functional groups in the molecule that can lead to one or more chain transfer reactions. Suitable chain transfer agents are described in detail, for example, by K. C. Berger and G. Brandrup in J. Brandrup, E. H. Immergut, Polymer Handbook, 3rd edition, John Wiley & Sons, New York, 1989, pp. II/81-II/141.

Suitable chain transfer agents are, for example, aldehydes. such as formaldehyde, acetaldehyde, propionaldehyde, n-butyraldehyde, isobutyraldehyde.

The following can also be used as chain transfer agents: formic acid, salts or esters thereof, such as ammonium formate, 2,5-diphenyl-1-hexene, hydroxylammonium sulfate, and hydroxylammonium phosphate.

Further suitable chain transfer agents are halogen compounds, e.g. alkyl halides such as tetrachloromethane, chloroform, bromotrichloromethane, bromoform, allyl bromide, and benzyl compounds such as benzyl chloride or benzyl bromide.

Further suitable chain transfer agents are allyl compounds, for example allyl alcohol, functionalized allyl ethers such as allyl ethoxylates, alkyl allyl ethers, or glyceryl monoallyl ethers.

Preferably, chain transfer agents used are compounds comprising sulfur in bonded form.

Compounds of this kind are, for example, inorganic hydrogensulfites, disulfites and dithionites or organic sulfides, disulfides, polysulfides, sulfoxides and sulfones. These include di-n-butyl sulfide, di-n-octyl sulfide, diphenyl sulfide, thiodiglycol, ethylthioethanol, diisopropyl disulfide, di-n-butyl disulfide, di-n-hexyl disulfide, diacetyl disulfide, diethanol sulfide, di-t-butyl trisulfide, dimethyl sulfoxide, dialkyl sulfide, dialkyl disulfide and/or diaryl sulfide.

Suitable polymerization chain transfer agents are also thiols (compounds comprising sulfur in the form of SH groups, also referred to as mercaptans). Preferred chain transfer agents are mono-, bi- and polyfunctional mercaptans, mercapto alcohols and/or mercaptocarboxylic acids. Examples of these compounds are allyl thioglycolates, ethyl thioglycolate, cysteine, 2-mercaptoethanol, 1,3-mercaptopropanol, 3-mercaptopropane-1,2-diol, 1,4-mercaptobutanol, mercaptoacetic acid, 3-mercaptopropionic acid, mercaptosuccinic acid, thioglycerol, thioacetic acid, thiourea and alkyl mercaptans, such as n-butyl mercaptan, n-hexyl mercaptan or n-dodecyl mercaptan.

Examples of bifunctional chain transfer agents comprising two sulfur atoms in bonded form are bifunctional thiols, for example dimercaptopropanesulfonic acid (sodium salt), dimercaptosuccinic acid, dimercapto-1-propanol, dimercaptoethane, dimercaptopropane, dimercaptobutane, dimercaptopentane, dimercaptohexane, ethylene glycol bisthioglycolates and butanediol bis(thioglycolate). Examples of polyfunctional chain transfer agents are compounds comprising more than two sulfur atoms in bonded form. Examples thereof are trifunctional and/or tetrafunctional mercaptans.

All the chain transfer agents mentioned can be used individually or in combination with one another.

Typically, the chain transfer agent is either partly added to the initial charge, i.e. before the actual polymerization, or is added in its entirety in step b2) continuously to the polymerization mixture via one of the feeds.

The amount of the chain transfer agent and the way in which it is added to the reaction mixture have a strong influence on the mean molecular weight of the polymer composition. When a smaller amount of chain transfer agent is used and/or when the addition takes place for the most part or entirely during the polymerization (step b2), this generally leads to a greater mean molecular weight than when greater amounts of chain transfer agent are used and/or the chain transfer agent is used partly in the initial charge.

The ratio of the polyether component PE) used to prepare the polymer composition to the monomer composition M) used is preferably within a range from 1.0:0.8 to 1.0:5.

Preferably, the amount of polyether component PE) in the initial charge in step b1) is 10% to 100% by weight, more preferably 25% to 100% by weight and especially 30% to 100% by weight, based on the total weight of the polyether component PE) used for polymerization.

Preferably, the content of solvent in the initial charge in step b1) is not more than 90% by weight, based on the total weight of the feedstocks present in the first fraction. More preferably, the content of solvent in the initial charge in step b1) is not more than 75% by weight, especially not more than 70% by weight, based on the total weight of the feedstocks present in the initial charge. The amount of solvent changes generally only by a few percent by weight over the entire course of the process.

Typically, solvents S) having a boiling point at standard pressure (1 bar) of below 240° C. are used. Preferably, the solvent S) is selected from water, ethylene glycol, ethylene glycol mono($C_1$-$C_4$-alkyl) ethers, ethylene glycol di($C_1$-$C_4$-alkyl) ethers, 1,2-propylene glycol, 1,2-propylene glycol mono($C_1$-$C_4$-alkyl) ethers, 1,2-propylene glycol di($C_1$-$C_4$-alkyl) ethers, dipropylene glycol and mixtures thereof. More preferably, the solvent S) is selected from ethylene glycol, 1,2-propylene glycol, dipropylene glycol and mixtures thereof. In a specific execution, the solvent S) is selected from mixtures of water with at least one water-miscible solvent, preferably selected from ethylene glycol, 1,2-propylene glycol and dipropylene glycol, with the proviso that the mixture comprises not more than 10% by weight of water. In a further specific execution, the solvent S) is selected from 1,2-propylene glycol, dipropylene glycol and mixtures thereof.

In a specific variant, the initial charge provided in step b1) does not comprise any solvent. This is only added in step b2) via at least one of the feeds. In a very specific variant, no solvent is initially charged and no solvent is added over the entire course of the process.

Preferably, the polymer compositions obtained after the polymerization has ended (step b3)) are transferred into a suitable vessel and optionally cooled directly to ambient temperature (20° C.).

In general, the polymer composition obtained by the above-described process already has a gel-like consistency. If desired, the rheological properties of the polymer composition can be adjusted, for example, through the addition of solvents and/or thickeners. Suitable thickeners are described hereinafter under f).

The polymer composition used in accordance with the invention is preferably transparent, meaning that it has a transparency ($T_L$) of at least 85%, especially of at least 90%, based on the transparency of water.

The polymer composition used in accordance with the invention preferably has a viscosity within a range from about 600 to 10 000 000 mPa·s, more preferably from 1000 to 1 000 000 mPa·s, especially from 2000 to 500 000 mPa·s at 20° C. The viscosity at 20° C. and the viscosity profile as a function of temperature for the samples to be examined was examined by means of a rotary rheometer (DHR-1 from TA Instruments with Peltier system, plate/plate geometry, Ø 40 mm, h=1 mm) at temperatures of 20° C. to 80° C. Temperature ramp ($\gamma$=1% with $M_{min}$=100 µNm). Measurement temperature(s) of 80° C. to 20° C. and back, two runs each (cooling/heating rate 2 K/min). Measurement time 30 min per run.

The polymer composition used in accordance with the invention preferably has a content of acid groups of more than 1 mmol/g, more preferably of more than 1.3 mmol/g. The inventive polymer composition preferably has a content of acid groups of not more than 15 mmol/g. The inventive polymer composition especially has a content of acid groups of 1.5 mmol/g to 15 mmol/g.

The polymer composition used in accordance with the invention preferably has a content of acid groups of 3 mmol/g to 8 mmol/g.

None, some or all of the acid groups of the polymer composition used in accordance with the invention may be neutralized. Preferably, none or only some of the acid groups in the inventive polymer composition are neutralized.

The acid groups of the inventive polymer composition are preferably in non-neutralized form.

Preferably, the polymer composition has a solubility in water at 40° C. and a pH of 8 of at least 5 g/l.

The weight-average molecular weight $M_w$ of the inventive polymer composition, determined by means of gel permeation chromatography (GPC) using neutralized polyacrylic acid as polymer standard, is preferably 1000 to 70 000 daltons.

Formulations for Machine Dishwashing

The polymer composition used in accordance with the invention is effective both as a surfactant and as a cobuilder. Examples of inventive formulations comprising the polymer composition for machine dishwashing thus comprise machine dishwashing detergents, rinse aids and machine dishwashing detergents with rinse aid function. The formulations at room temperature (20° C.) are especially in gel form, in solid form, or partly in gel form and partly in solid form.

The inventive formulations for machine dishwashing are especially notable for excellent deposit-inhibiting action when used in the rinse cycle of the machine dishwasher (i.e. it acts as an incrustation inhibitor). They have inhibiting action with respect to both inorganic and organic deposits. The inorganic deposits are especially calcium and magnesium phosphate, calcium and magnesium carbonate, calcium and magnesium silicate and/or calcium and magnesium phosphonate, which arise from the calcium and magnesium salts present in the water and the builders present in standard dishwashing detergents. The organic deposits are especially soil constituents from the rinse liquor, for example protein, starch and fat deposits. The inventive formulations for machine dishwashing are also effective against carry-over deposits, which originate from the residual water in the bottom of the machine dishwasher and comprise, inter alia, dishwashing composition residues and possibly also soil residues from the previous wash cycle of the machine dishwasher.

The constituents of the polymer composition also support the cleaning performance of the overall formulation, by detaching and dispersing the soil.

The inventive formulation for machine dishwashing preferably comprises the following constituents:
a) at least one inventive polymer composition in gel form,
b) at least one builder (also referred to as sequestrant, builder material, complexing agent, chelator, chelating agent or softener),
c) optionally at least one enzyme,
d) optionally at least one bleach,
e) water,
f) optionally at least one thickener, and
g) optionally at least one additive, preferably selected from the following additives other than a): surfactants, bases, corrosion inhibitors, defoamers, dyes, fragrances, fillers, solubilizers and organic solvents.

The inventive formulation in gel form for machine dishwashing comprises, based on the total weight of the formulation, preferably:
a) 0.1% to 50% by weight of at least one inventive polymer composition in gel form,
b) 5% to 90% by weight of at least one builder and/or cobuilder,
c) 0% to 8% by weight of at least one enzyme,
d) 0% to 30% by weight of at least one bleach,
e) 0.1% to 90% by weight of water,
f) 0% to 8% by weight of at least one thickener,
g) 0% to 25% by weight of at least one further additive,
with the proviso that the weights of components a) to g) add up to 100% by weight.

In a preferred embodiment, the inventive formulation in gel form for machine dishwashing comprises at least one enzyme.

The inventive formulation for machine dishwashing comprises, based on the total weight of the formulation, preferably:
a) 2% to 40% by weight of at least one inventive polymer composition in gel form,
b) 5% to 80% by weight of at least one builder and/or cobuilder,
c) 0.1% to 6% by weight of at least one enzyme,
d) 0% to 30% by weight of at least one bleach,
e) 0.1% to 80% by weight of water,
f) 0% to 6% by weight of at least one thickener,
g) 0% to 25% by weight of at least one further additive,
with the proviso that the weights of components a) to g) add up to 100% by weight.

More preferably, the inventive formulation for machine dishwashing comprises, based on the total weight of the formulation:
a) 0.12% to 30% by weight of at least one inventive polymer composition in gel form,
b) 5% to 75% by weight of at least one builder and/or cobuilder,
c) 0.1% to 6% by weight of at least one enzyme,
d) 0% to 25% by weight of at least one bleach,
e) 0.1% to 80% by weight of water,
f) 0.1% to 5% by weight of at least one thickener,
g) 0% to 25% by weight of at least one further additive,
with the proviso that the weights of components a) to g) add up to 100% by weight.

The polymer composition a) may be incorporated into the formulation or may be present in the overall formulation in a separate region as a clear gel component separately from the other components (for example divided by a film, for example of polyvinyl alcohol).

The detergent formulations may be in the form of tablets or entirely liquid formulations. However, it is also possible for containers produced with films or shaped bodies, having 1 to 6 individual sections of equal or different size, to be present. These may independently be filled with powder, pellets, solids or liquids. The polymer composition a) is preferably dispensed in a separate compartment and is present therein as a clear gel. The polymer composition a) may additionally be thickened or colored.

Component a)

With regard to inventive polymer compositions suitable and preferred as component a), reference is made to the details above.

Component b)

Builders and cobuilders, which are sometimes also referred to as sequestrants, builder materials, complexing agents, chelators, chelating agents or softeners, bind alkaline earth metals and other water-soluble metal salts. They help to break up soil, disperse soil components, help to detach soil and in some cases themselves have a washing effect. In addition, when they are solid and are used in pulverulent formulations, they keep the powder free-flowing.

Suitable builders may be either organic or inorganic in nature. Examples are aluminosilicates, carbonates, phosphates and polyphosphates, polycarboxylic acids, polycarboxylates, hydroxycarboxylic acids, phosphonic acids, e.g. hydroxyalkylphosphonic acids, phosphonates, aminopolycarboxylic acids and salts thereof, and polymeric compounds containing carboxylic acid groups and salts thereof.

Crystalline silicates suitable as builders are, for example, disilicates or sheet silicates, e.g. 5-$Na_2Si_2O_5$ or β—$Na_2Si_2O_5$ (SKS 6 or SKS 7). The silicates can be used in the form of their alkali metal, alkaline earth metal or ammonium salts, preferably as sodium, lithium and magnesium silicates. Amorphous silicates, for example sodium metasilicate which has a polymeric structure, or amorphous disilicate (Britesil® H 20, manufacturer: Akzo), are likewise usable. Among these, preference is given to sodium disilicate.

Suitable inorganic builder substances based on carbonate are carbonates and hydrogencarbonates. These can be used in the form of their alkali metal, alkaline earth metal or ammonium salts. Preference is given to using sodium, lithium and magnesium carbonates or sodium, lithium and magnesium hydrogencarbonates, especially sodium carbonate and/or sodium hydrogencarbonate.

Customary phosphates used as inorganic builders are alkali metal orthophosphates and/or polyphosphates, for example pentasodium triphosphate.

Suitable organic builders are, for example, $C_4$-$C_{30}$-di-, -tri- and -tetracarboxylic acids, for example succinic acid, propanetricarboxylic acid, butanetetracarboxylic acid, cyclopentanetetracarboxylic acid, and alkyl- and alkenyl-succinic acids having $C_2$-$C_{20}$-alkyl or -alkenyl radicals.

Suitable organic builders are also hydroxycarboxylic acids and polyhydroxycarboxylic acids (sugar acids). These include $C_4$-$C_{20}$-hydroxycarboxylic acids, for example malic acid, tartaric acid, gluconic acid, mucic acid, lactic acid, glutaric acid, citric acid, tartronic acid, glucoheptonic acid, lactobionic acid, and sucrosemono-, -di- and -tricarboxylic acid. Among these, preference is given to citric acid and salts thereof.

Suitable organic builders are also phosphonic acids, for example hydroxyalkylphosphonic acids, aminophosphonic acids and the salts thereof. These include, for example, phosphonobutanetricarboxylic acid, aminotris(methylenephosphonic acid), ethylenediaminetetraethylenephosphonic acid, hexamethylenediaminetetramethylenephosphonic acid, diethylenetriaminepentamethylenephosphonic acid, morpholinomethanediphosphonic acid, 1-hydroxy-$C_1$-$C_{10}$-alkyl-1,1-diphosphonic acids such as 1-hydroxyethane-1,1-diphosphonic acid. Among these, preference is given to 1-hydroxyethane-1,1-diphosphonic acid and salts thereof.

Suitable organic builders are additionally aminopolycarboxylic acids, such as nitrilotriacetic acid (NTA), nitrilomonoacetic dipropionic acid, nitrilotripropionic acid, β-alaninediacetic acid (β-ADA), ethylenediaminetetraacetic acid (EDTA), diethylenetriaminepentaacetic acid, 1,3-propylenediaminetetraacetic acid, 1,2-propylenediaminetetraacetic acid, N-(alkyl)ethylenediaminetriacetic acid, N-(hydroxyalkyl)ethylenediaminetriacetic acid, ethylenediaminetriacetic acid, cyclohexylene-1,2-diaminetetraacetic acid, iminodisuccinic acid, ethylenediaminedisuccinic acid, serinediacetic acid, isoserinediacetic acid, L-asparaginediacetic acid, L-glutaminediacetic acid, methylglycinediacetic acid (MGDA), and the salts of the aforementioned aminopolycarboxylic acids. Among these, preference is given to L-glutaminediacetic acid, methylglycinediacetic acids and salts thereof.

Suitable organic builders are additionally polymeric compounds containing carboxylic acid groups, such as acrylic acid homopolymers. These preferably have a number-average molecular weight in the range from 800 to 70 000 g/mol, more preferably from 900 to 50 000 g/mol, particularly from 1000 to 20 000 g/mol, especially 1000 to 10 000 g/mol. The term "acrylic acid homopolymer" also comprises polymers in which some or all of the carboxylic acid groups are in neutralized form. These include acrylic acid homopolymers in which some or all of the carboxylic acid groups are in the form of alkali metal salts or ammonium salts. Preference is given to acrylic acid homopolymers in which the carboxylic acid groups are protonated or in which some or all of the carboxylic acid groups are in the form of sodium salts.

Suitable polymeric compounds containing carboxylic acid groups are also oligomaleic acids, as described, for example, in EP-A 451 508 and EP-A 396 303.

Suitable polymeric compounds containing carboxylic acid groups are also terpolymers of unsaturated $C_4$-$C_8$-dicarboxylic acids, where the polymerized comonomers may include monoethylenically unsaturated monomers from group (i) specified below in amounts of up to 95% by weight, from group (ii) in amounts of up to 60% by weight and from group (iii) in amounts of up to 20% by weight. Suitable unsaturated $C_4$-$C_8$-dicarboxylic acids in this context are, for example, maleic acid, fumaric acid, itaconic acid and citraconic acid. Preference is given to maleic acid. Group (i) comprises monoethylenically unsaturated $C_3$-$C_8$-monocarboxylic acids, for example acrylic acid, methacrylic acid, crotonic acid and vinylacetic acid. From group (i), preference is given to using acrylic acid and methacrylic acid. Group (ii) comprises monoethylenically unsaturated $C_2$-$C_{22}$-olefins, vinyl alkyl ethers having $C_1$-$C_8$-alkyl groups, styrene, vinyl esters of $C_1$-$C_8$-carboxylic acids, (meth)acrylamide and vinylpyrrolidone. From group (ii), preference is given to using $C_2$-$C_6$-olefins, vinyl alkyl ethers having $C_1$-$C_4$-alkyl groups, vinyl acetate and vinyl propionate. If the polymers of group (ii) comprise vinyl esters in polymerized form, they may also be present partly or fully hydrolyzed to vinyl alcohol structural units. Suitable co- and terpolymers are known, for example, from U.S. Pat. No. 3,887,806 and DE-A 4313909. Group (iii) comprises (meth)acrylic esters of $C_1$-$C_8$ alcohols, (meth)acrylonitrile, (meth)acrylamides of $C_1$-$C_8$ amines, N-vinylformamide and N-vinylimidazole.

Suitable polymeric compounds containing carboxylic acid groups are also homopolymers of the monoethylenically unsaturated $C_3$-$C_8$-monocarboxylic acids, for example acrylic acid, methacrylic acid, crotonic acid and vinylacetic acid, especially of acrylic acid and methacrylic acid, copolymers of dicarboxylic acids, for example copolymers of maleic acid and acrylic acid in a weight ratio of 10:90 to 95:5, more preferably those in a weight ratio of from 30:70 to 90:10 with molar masses of from 1000 to 150 000; terpolymers of maleic acid, acrylic acid and a vinyl ester of a $C_1$-$C_3$-carboxylic acid in a weight ratio of from 10 (maleic acid):90 (acrylic acid+vinyl ester) to 95 (maleic acid):10 (acrylic acid+vinyl ester), where the weight ratio of acrylic acid to the vinyl ester may vary within the range from 30:70 to 70:30; copolymers of maleic acid with $C_2$-$C_8$-olefins in a molar ratio of from 40:60 to 80:20, particular preference being given to copolymers of maleic acid with ethylene, propylene or isobutene in a molar ratio of 50:50.

Suitable polymeric compounds containing carboxylic acid groups are also copolymers of 50% to 98% by weight of ethylenically unsaturated weak carboxylic acids with 2% to 50% by weight of ethylenically unsaturated sulfonic acids, as described, for example, in EP-A-0877002. Suitable weak ethylenically unsaturated carboxylic acids are especially $C_3$-$C_6$-monocarboxylic acids, such as acrylic acid and methacrylic acid. Suitable ethylenically unsaturated sulfonic acids are 2-acetylamidomethyl-1-propanesulfonic acid, 2-methacrylamido-2-methyl-1-propanesulfonic acid, 2-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 3-sulfopropyl methacrylate, sulfomethylacrylamide, sulfomethylmethacrylamide and salts of these acids. The copolymers may also comprise, in copolymerized form, 0 to 30% by weight of ethylenically unsaturated $C_4$-$C_8$-dicarboxylic acids, such as maleic acid, and 0 to 30% by weight of at least one monomer which is copolymerizable with the aforementioned monomers. The latter are, for example, $C_1$-$C_4$-alkyl esters of (meth)acrylic acid, $C_1$-$C_4$-hydroxyalkyl esters of (meth)acrylic acid, acrylamide, alkyl-substituted acrylamide, N,N-dialkyl-substituted acrylamide, vinylphosphonic acid, vinyl acetate, allyl alcohols, sulfonated allyl alcohols, styrene and other vinylaromatics, acrylonitrile, N-vinylpyrrolidone, N-vinylformamide, N-vinylmidazole or N-vinylpyridine. The weight-average molecular weight of these copolymers is within the range from 3000 to 50 000. Particularly suitable copolymers are those with about 77% by weight of at least one ethylenically unsaturated $C_3$-$C_6$-monocarboxylic acid and about 23% by weight of at least one ethylenically unsaturated sulfonic acid.

Graft polymers of unsaturated carboxylic acids onto low molecular weight carbohydrates or hydrogenated carbohydrates (cf. U.S. Pat. No. 5,227,446, DE-A 4415623 and DE-A 4313909) are likewise suitable. Suitable unsaturated carboxylic acids in this context are, for example, maleic acid, fumaric acid, itaconic acid, citraconic acid, acrylic acid, methacrylic acid, crotonic acid and vinylacetic acid and also mixtures of acrylic acid and maleic acid, which are grafted on in amounts of 40% to 95% by weight, based on the component to be grafted. For modification, it is additionally possible for up to 30% by weight, based on the component to be grafted, of further monoethylenically unsaturated monomers to be present in polymerized form. Suitable modifying monomers are the abovementioned monomers of groups (ii) and (iii). Suitable graft bases are degraded polysaccharides, for example acidically or enzymatically degraded starches, inulins or cellulose, protein hydrolyzates and reduced (hydrogenated or hydrogenatingly aminated) degraded polysaccharides, for example mannitol, sorbitol, aminosorbitol and N-alkylglucamine, as are polyalkylene glycols with molar masses of up to $M_w$=5000, for example polyethylene glycols, ethylene oxide/propylene oxide or ethylene oxide/butylene oxide or ethylene oxide/propylene oxide/butylene oxide block copolymers and alkoxylated mono- or polyhydric $C_1$-$C_{22}$ alcohols (cf. U.S. Pat. No. 5,756,456).

Likewise suitable are polyglyoxylic acids, as described, for example, in EP-B 001004, U.S. Pat. No. 5,399,286, DE-A-4106355 and EP-A-656914. The end groups of the polyglyoxylic acids may have different structures.

Additionally suitable are polyamidocarboxylic acids and modified polyamidocarboxylic acids; these are, for example, known from EP-A-454126, EP-B-511037, WO-A-94/01486 and EP-A-581452.

Polyaspartic acids or cocondensates of aspartic acid with further amino acids, $C_4$-$C_{25}$ mono- or -dicarboxylic acids and/or $C_4$-$C_{25}$ mono- or -diamines can also be used as polymeric compounds containing carboxylic acid groups. Particular preference is given to using polyaspartic acids which have been prepared in phosphorus acids and have been modified with $C_6$-$C_{22}$ mono- or -dicarboxylic acids or with $C_6$-$C_{22}$ mono- or -diamines.

Among the polymeric compounds containing carboxylic acid groups, polyacrylic acids are preferred, including in partly or fully neutralized form.

Suitable organic builders are also iminodisuccinic acid, oxydisuccinic acid, aminopolycarboxylates, alkyl polyaminocarboxylates, aminopolyalkylenephosphonates, polyglutamates, hydrophobically modified citric acid for example agaric acid, poly-α-hydroxyacrylic acid, N-acylethylenediamine triacetates such as lauroylethylenediamine triacetate and alkylamides of ethylenediaminetetraacetic acid, such as EDTA tallow amide.

In addition, it is also possible to use oxidized starches as organic builders.

Preference is given to using, as component b), a mixture of different builders.

Component c)

The enzymes are preferably selected from hydrolases, such as proteases, esterases, glucosidases, lipases, amylases, cellulases, mannanases, other glycosyl hydrolases and mixtures of the aforementioned enzymes. AN these hydrolases contribute to soil dissolution and removal from protein-, grease- or starch-containing stains. It is also possible to use oxireductases for bleaching. Of particularly good suitability are active enzymatic ingredients obtained from bacterial strains or fungi such as *Bacillus subtilis, Bacillus licheniformis, Streptomyceus griseus* and *Humicola insolens*.

Suitable hydrolases are, for example, α-glucosidases (EC number 3.2.1.20), proteases (Ovozyme® (from Novozymes); EC number 3.2.1.20), amylases [Purastar® (from Genencor), Termamyl® (from Novozymes), Stainzyme® (from Novozymes), Duramyl® (from Novozymes)], mannanases [Purabrite® (from Genencor), Mannastar® (from Genencor), Mannaway® (from Novozymes)] and cellulases [Carezyme® (from Novozymes), Celluzyme® (from Novozymes), endolase, Puradax® (from Genencor)]. The suitable amylases include especially α-amylases (EC number 3.2.1.1), isoamylases, pullulanases and pectinases. Cellulases used are preferably cellobiohydrolases, endoglucanases and β-glucosidases, which are also called cellobiases, or mixtures of these. Since different cellulase types differ by their CMCase and avicelase activities, it is possible to establish the desired activities by means of selected mixtures of the cellulases.

Suitable lipases are esterases, such as Lipex and Lipolase. Examples of lipolytic enzymes are known cutinases.

Peroxidases or oxidases have also been found to be suitable in some cases.

Preferably, the inventive dishwashing composition comprises at least one protease and/or amylase.

Particular preference is given to protease and/or amylase-containing mixtures. Preferred proteases in the aforementioned mixtures are proteases of the subtilisin type (Savinase, etc.; EC number 3.4.21.62).

The enzymes may be adsorbed on carrier substances in order to protect them from premature breakdown.

Optionally, the inventive dishwashing detergent may also comprise enzyme stabilizers, for example calcium propionate, sodium formate or boric acids or salts thereof, and/or antioxidants.

Component d)

The bleaches d) are preferably bleach systems which, as well as bleaches, optionally also comprise bleach activators, bleach catalysts and/or bleach stabilizers.

Suitable bleaches are, for example, percarboxylic acids, for example diperoxododecanedicarboxylic acid, phthalimidopercaproic acid or monoperoxophthalic acid or -terephthalic acid, salts of percarboxylic acids, for example sodium percarbonate, adducts of hydrogen peroxide onto inorganic salts, for example sodium perborate monohydrate, sodium perborate tetrahydrate, sodium carbonate perhydrate or sodium phosphate perhydrate, adducts of hydrogen peroxide onto organic compounds, for example urea perhydrate, or of inorganic peroxo salts, for example alkali metal persulfates or peroxodisulfates.

Suitable bleach activators are, for example, polyacylated sugars, e.g. pentaacetylglucose; acyloxybenzenesulfonic acids and the alkali metal and alkaline earth metal salts thereof, e.g. sodium p-nonanoyloxybenzenesulfonate or sodium p-benzoyloxybenzenesulfonate; N,N-diacylated and N,N,N',N'-tetraacylated amines, e.g. N,N,N',N'-tetraacetylmethylenediamine and -ethylenediamine (TAED), N,N-diacetylaniline, N,N-diacetyl-p-toluidine or 1,3-diacylated hydantoins such as 1,3-diacetyl-5,5-dimethylhydantoin; N-alkyl-N-sulfonylcarbonamides, e.g. N-methyl-N-mesylacetamide or N-methyl-N-mesylbenzamide; N-acylated cyclic hydrazides, acylated triazoles or urazoles, e.g. monoacetylmaleic hydrazide; O,N,N-trisubstituted hydroxylamines, e.g. O-benzoyl-N,N-succinylhydroxylamine, O-acetyl-N,N-succinylhydroxylamine or O,N,N-triacetylhydroxylamine; N,N'-diacylsulfurylamides, e.g. N,N'-dimethyl-N,N'-diacetylsulfurylamide or N,N'-diethyl-N,N'-dipropionylsulfurylamide; acylated lactams, for example acetylcaprolactam, octanoylcaprolactam, benzoylcaprolactam or carbonylbiscaprolactam; anthranil derivatives, for example 2-methylanthranil or 2-phenylanthranil; triacyl cyanurates, e.g. triacetyl cyanurate or tribenzoyl cyanurate; oxime esters and bisoxime esters, for example O-acetylacetone oxime or bisisopropyl iminocarbonate; carboxylic anhydrides, e.g. acetic anhydride, benzoic anhydride, m-chlorobenzoic anhydride or phthalic anhydride; enol esters, for example isopropenyl acetate; 1,3-diacyl-4,5-diacyloxylmidazolines, e.g. 1,3-diacetyl-4,5-diacetoxyimidazoline; tetraacetylglycoluril and tetrapropionylglycoluril; diacylated 2,5-diketopiperazines, e.g. 1,4-diacetyl-2,5-diketopiperazine; ammonium-substituted nitriles, for example N-methylmorpholinioacetonitrile methylsulfate; acylation products of propylenediurea and 2,2-dimethylpropylenediurea, e.g. tetraacetylpropylenediurea; α-acyloxypolyacylmalonamides, e.g. α-acetoxy-N,N'-diacetylmalonamide; diacyldioxohexahydro-1,3,5-triazines, z.B. 1,5-diacetyl-2,4-dioxohexahydro-1,3,5-triazine; benz-(4H)-1,3-oxazin-4-ones with alkyl radicals, e.g. methyl, or aromatic radicals, e.g. phenyl, in the 2 position.

A bleach system composed of bleaches and bleach activators may optionally also comprise bleach catalysts. Suitable bleach catalysts are, for example, quaternized imines and sulfonimines, described, for example, in U.S. Pat. No. 5,360,569 and EP-A 453 003. Particularly effective bleach catalysts are manganese complexes, described, for example, in WO-A 94/21777. In the case that they are used in the washing and cleaning compositions, such compounds are incorporated at most in amounts up to 1.5% by weight, especially up to 0.5% by weight, and in the case of very active manganese complexes in amounts up to 0.1% by weight. In addition to the described bleach system composed of bleaches, bleach activators and optionally bleach catalysts, it is also possible to use systems with enzymatic peroxide release or photoactivated bleach systems for the inventive washing and cleaning compositions.

Component f)

The polymer compositions used in accordance with the invention are suitable even alone for modifying the rheological properties for the purposes of thickening.

In order to impart the desired viscosity to the formulation used in accordance with the invention for machine dishwashing, it is additionally possible to use at least one thickener f).

In principle, any known thickeners (rheology modifiers) are suitable, provided that they do not exert any adverse effect on the action of the dishwashing composition. Suitable thickeners may be of natural origin or synthetic in nature.

Examples of thickeners of natural origin are xanthan, carob seed flour, guar flour, carrageenan, agar, tragacanth, gum arabic, alginates, modified starches such as hydroxyethyl starch, starch phosphate esters or starch acetates, dextrins, pectins, and cellulose derivatives such as carboxymethyl cellulose, hydroxyethyl cellulose, hydroxypropyl cellulose, hydroxypropylmethyl cellulose, methyl cellulose and the like.

Thickeners of natural origin are also inorganic thickeners, such as polysilicic acids and clay minerals, e.g. sheet silicates, and also the silicates specified for the builders.

Examples of synthetic thickeners are polyacrylic and polymethacrylic compounds, such as (partly) crosslinked homopolymers of acrylic acid, for example with an allyl ether of sucrose or pentaerythritol or homopolymers of acrylic acid crosslinked with propylene (carbomer), for example the Carbopol® products from BF Goodrich (e.g. Carbopol® 676, 940, 941, 934 and the like) or the Polygel® products from 3V Sigma (e.g. Polygel® DA), copolymers of ethylenically unsaturated mono- or dicarboxylic acids, for example terpolymers of acrylic acid, methacrylic acid or maleic acid with methyl or ethyl acrylate and a (meth) acrylate which is derived from long-chain ethoxylated alcohols, for example the Acusol® products from Rohm & Haas (e.g. Acusol® 820 or 1206A), copolymers of two or more monomers, which are selected from acrylic acid, methacrylic acid and their $C_1$-$C_4$-alkyl esters, for example copolymers of methacrylic acid, butyl acrylate and methyl methacrylate or of butyl acrylate and methyl methacrylate, for example the Aculyn® and Acusol® products from Rohm & Haas (e.g. Aculyn® 22, 28 or 33 and Acusol® 810, 823 and 830), or crosslinked high molecular weight acrylic acid copolymers, for example copolymers, crosslinked with an allyl ether of sucrose or pentaerythritol, of $C_{10}$-$C_{30}$-alkyl acrylates with one or more comonomers which are selected from acrylic acid, methacrylic acid and their $C_1$-$C_4$-alkyl esters (e.g. Carbopol® ETD 2623, Carbopol® 1382 or Carbopol® AQUA 30 from Rohm & Haas).

Examples of synthetic thickeners are also reaction products of maleic acid polymers with ethoxylated long-chain alcohols, for example the Surfonic L series from Texaco Chemical Co. or Gantrez AN-119 from ISP; polyethylene glycols, polyamides, polyimines and polycarboxylic acids.

Mixtures of the abovementioned thickeners are also suitable.

Preferred thickeners are xanthans and the abovementioned polyacrylic and polymethacrylic compounds.

Component g)

Suitable additional surfactants g) other than component a) are anionic surfactants, nonionic surfactants, cationic surfactants, amphoteric surfactants and mixtures thereof.

Typical examples of anionic surfactants are soaps, alkylsulfonates, alkylbenzenesulfonates, olefinsulfonates, methyl ester sulfonates, sulfo fatty acids, alkyl sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, for example acyl lactylates, acyl tartrates, acyl glutamates and acyl aspartates, alkyl oligoglucoside sulfates, alkylglucose carboxylates, protein fatty acid condensates and alkyl (ether) phosphates.

The further additional nonionic surfactants include, for example:
- glyceryl esters, for example glyceryl monostearate,
- sugar surfactants, sorbitol esters, for example sorbitan fatty acid esters (sorbitan monooleate, sorbitan tristearate), polyoxyethylenesorbitan fatty acid esters, alkyl polyglycosides, N-alkylgluconamides,
- alkyl methyl sulfoxides,
- alkyldimethylphosphine oxides, for example tetradecyldimethylphosphine oxide.

Suitable amphoteric surfactants are, for example, alkyl betaines, alkylamidopropyl betaines, alkyl sulfobetaines, alkyl glycinates, alkyl carboxyglycinates, alkyl amphoacetates or alkyl amphopropionates, alkyl amphodiacetates or alkyl amphodipropionates. For example, it is possible to use cocodimethylsulfopropyl betaine, lauryl betaine, cocamidopropyl betaine, sodium cocamphopropionate or tetradecyldimethylamine oxide.

The cationic surfactants include, for example, quaternized ammonium compounds, especially alkyltrimethylammonium and dialkyldimethylammonium halides and alkylsulfates, and also pyridine and imidazoline derivatives, especially alkylpyridinium halides. For example, it is possible to use behenyl- or cetyltrimethylammonium chloride.

Suitable organic solvents g) are selected from mono- or polyhydric alcohols, alkanolamines and glycol ethers. They are preferably selected from ethanol, n- or i-propanol, butanols, glycol, propane- or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol mono methyl or ethyl ether, diisopropylene glycol monomethyl or monoethyl ether, methoxy-, ethoxy- or butoxytriglycol, i-butoxyethoxy-2-propanol, 3-methyl-3-methoxybutanol, propylene glycol t-butyl ether and mixtures of these solvents.

Useful foam inhibitors or defoamers g) include, for example, soaps, paraffins or silicone oils, which may optionally be applied to support materials.

Suitable bases g) are on alkali metal hydroxides, alkaline earth metal hydroxides, alkali metal carbonates, alkaline earth metal carbonates, ammonium carbonate, alkali metal hydrogencarbonates, alkaline earth metal hydrogencarbonates, ammonium hydrogencarbonate and mixtures thereof. Preference is given to using sodium, lithium and magnesium carbonates or sodium, lithium and magnesium hydrogencarbonates, especially sodium carbonate and/or sodium hydrogencarbonate.

The present application further provides a method for cleaning dishware in a machine dishwasher, using inventive formulations comprising the polymer composition a) for machine dishwashing, wherein the formulations are preferably dosed into the interior of a machine dishwasher during the progress of a dishwashing program, prior to commencement of the main wash cycle or in the course of the main wash cycle. The dosage or introduction of the formulations used in accordance with the Invention into the interior of the machine dishwasher can be effected manually, but the composition is preferably dosed into the interior of the machine dishwasher by means of a detergent compartment of the machine dishwasher. The formulations used in accordance with the invention exhibit their advantageous cleaning properties especially in low-temperature cleaning methods as well. These processes are conducted at temperatures of not more than 55° C., preferably of not more than 50° C. The inventive formulations are notable for good cleaning performance compared to conventional formulations for machine dishwashing. They are additionally suitable for improving drying in the course of machine dishwashing.

The invention is illustrated in detail by the figures described hereinafter and the examples. At the same time, the figures and examples should not be understood such that they restrict the invention.

In the figures and examples which follow, the following abbreviations are used:
EO: ethylene oxide
PO: propylene oxide
BO: butylene oxide
$M_n$: number-average molecular weight
$M_w$: weight-average molecular weight
PET: polyethylene terephthalate
$T_L$: transparency value
n.d.: not determined
rad/s: radiant per second
pphm: parts by weight per 100 parts by weight of monomer (parts per hundred monomer).

DESCRIPTION OF FIGURES

FIG. 1 shows the viscosity as a function of temperature for the gel from example 8 of table 1.

Figure 2:
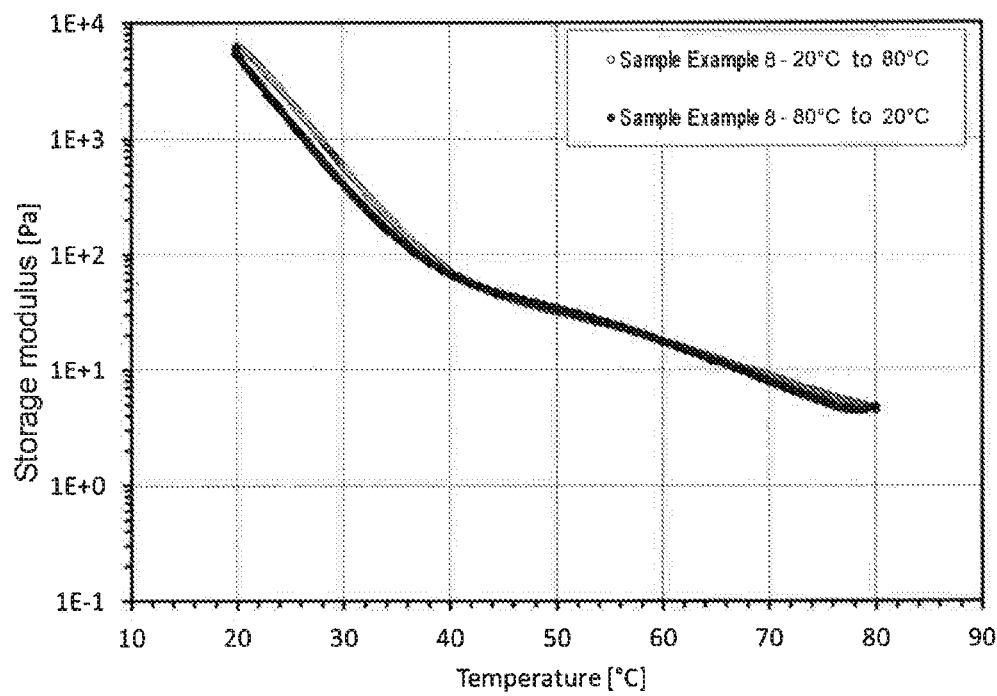
FIG. 2 shows the storage modulus as a function of temperature for the gel from example 8 of table 1.

FIG. 2 shows the storage modulus as a function of temperature for the gel from example 8 of table 1.

Figure 3:
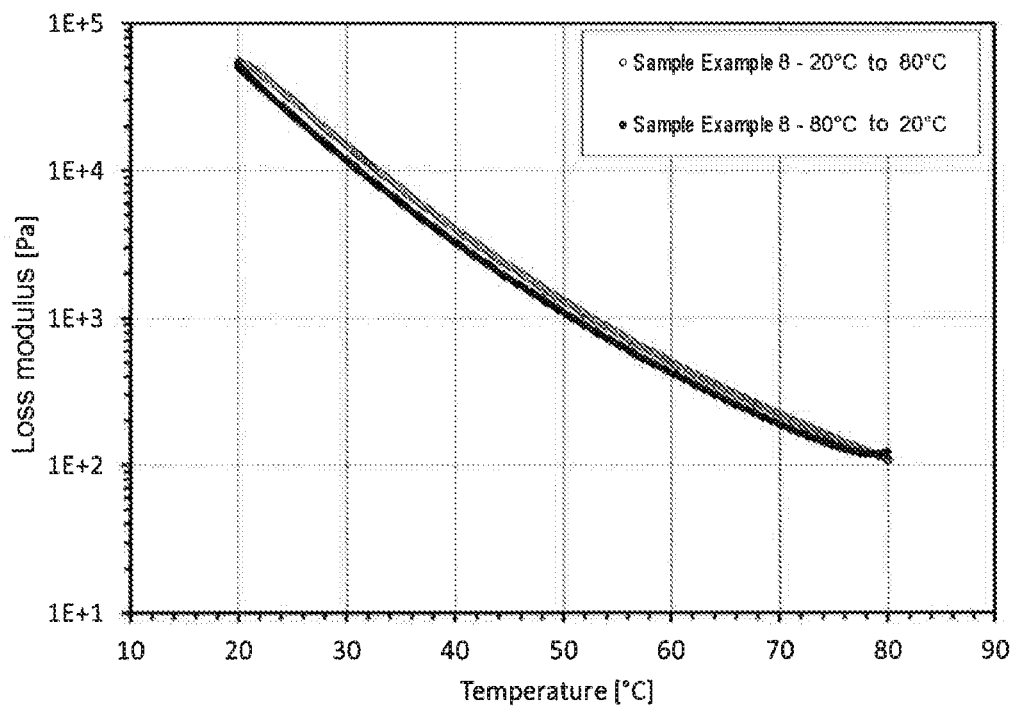
FIG. 3 shows the loss modulus as a function of temperature for the gel from example 8 of table 1.

FIG. 3 shows the loss modulus as a function of temperature for the gel from example 8 of table 1.

Figure 4:
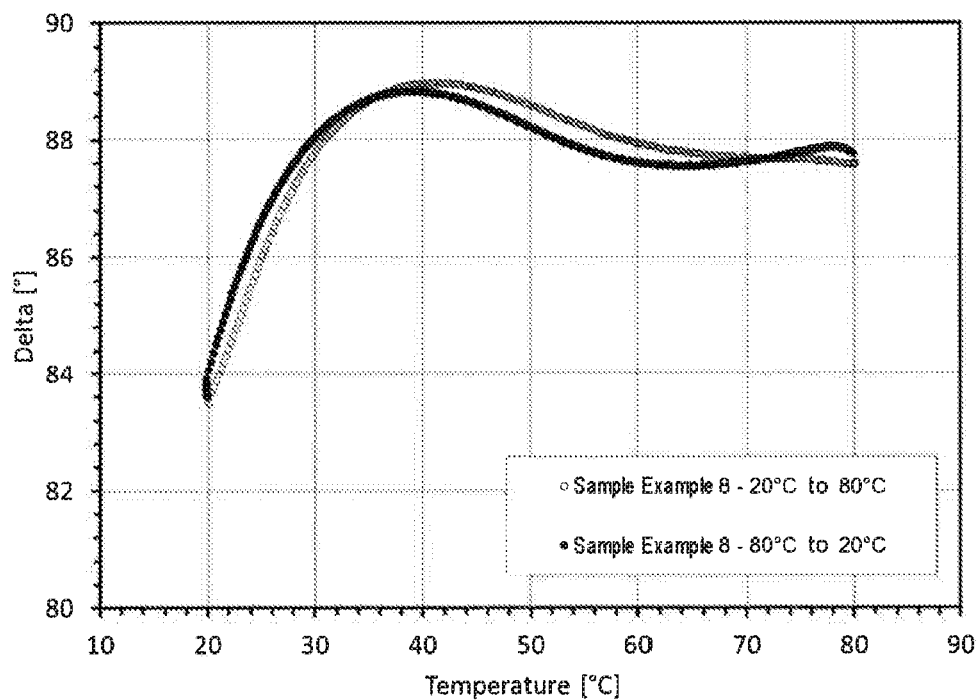
FIG. 4 shows the phase angle δ as a function of temperature for the gel from example 8 of table 1.

FIG. 4 shows the phase angle δ as a function of temperature for the gel from example 8 of table 1.

EXAMPLES

I) Analysis

I.a) Determination of Water Solubility

To determine water solubility, 5 g of the particular polymer composition were introduced into a 1 l beaker, and 900 ml of water which had been heated to 40° C. beforehand were added. The mixture was stirred with a magnetic stirrer at 40° C. for 20 minutes and the pH was adjusted to 8 with sodium hydroxide solution. Water-soluble polymer gels led to transparent or slightly cloudy solutions.

I.b) Determination of Weight-Average Molecular Weight ($M_w$):

The weight-average molecular weight of the polymer was determined by gel permeation chromatography (GPC). For this purpose, the following instruments and chromatography methods were used:
Standard: polyacrylic acid, neutralized
Eluent: 0.08 mol/l Tris, pH 7.0, +0.15 mol/l NaCl+0.01 mol/l NaN$_3$ in deionized water
Flow rate: 0.8 ml/min Column set: 1 precolumn (l=5 cm), 2 separation columns (l=30 cm each)
Column temperature: 35° C.
Detector: DRI (refractive index detector) Agilent 1100
I.c) Determination of Transparency:
The transparency of the specimens was determined via the light transmittance thereof ($T_L$) at a wavelength of 500 nm and at 20° C. The 100% reference used was water.

II) Preparation Examples

General Preparation Method:
A glass reactor equipped with three feeds, nitrogen inlet and an anchor stirrer was initially charged with the polyether component (PE), optionally the chain transfer agent (CTA) and optionally the solvent (S) in an amount according to table 1, purged with nitrogen for a couple of minutes and heated to 75° C. Subsequently, feeds 1 to 3 were added simultaneously to the initial charge at 75° C. and while stirring at 100 revolutions/minute within 4 hours. Feed 1 comprised monomer (M), feed 2 comprised an initiator (FRI) dissolved in a small amount of nonionic surfactant (PE) and/or solvent (S), and feed 3 optionally comprised a further amount of chain transfer agent (CTA). After the addition of feeds 1, 2 and 3, the mixture was stirred at 75° C. and at 100 revolutions/minute for a further hour for continued polymerization. Subsequently, the polymer was poured into a beaker and cooled immediately to room temperature.

For production of the inventive polymer compositions, the following feedstocks were used:
M1: acrylic acid
PE1: liquid nonionic surfactant; reaction product of 5.5 mol of EO, 2 mol of PO and 1 mol of tridecanol
PE2: liquid nonionic surfactant; reaction product of 7.8 mol of EO, 1.2 mol of BO and 1.0 mol of a mainly unbranched $C_9$-$C_{11}$ oxo alcohol
PE3: liquid polyether consisting of polyethylene glycol having a mean molar mass of 400 g/mol
PE4: solid nonionic surfactant consisting of a modified fatty alcohol polyglycol ether
PE5: $C_{13}C_{15}$ alcohol+9 EO+2 BuO
PE6: $C_6$ alcohol+6 EO (proceeding from hexylglycol or hexyldiglycol)
PE7: $C_{13}C_{15}$ oxo alcohol+8 EO+3.8 PO
CTA1: 2-ethylhexyl thioglycolate
CTA2: 2-mercaptoethanol
CTA3: $NaH_2PO_2$ (55% aqueous solution)
S1: propylene glycol
S2: dipropylene glycol
S3: water
S4: isopropanol
FRI1: tert-butyl peroxyneodecanoate (purity: 97%) (CAS No. 26748-41-4)
FRI2: tert-butyl peroxypivalate (purity: 75%) (CAS No. 927-07-1)
FRI3: 2,2'-azobis(2-methylpropionamidine)dihydrochloride (CAS No. 2997-92-4)

The inventive polymer compositions of examples 1 to 13 were prepared by the general preparation method described above. The monomer component (M1) used was acrylic acid. The acrylic acid and the particular polyether component (PE) were added in the proportions by weight stated in table 1, with varying amounts of the solvent (S), the initiator (FRI), and the chain transfer agent (CTA) in the polymer mixtures. The consistency and analytical parameters of the resulting polymer compositions are summarized in table 2 below.

TABLE 1

| | Initial charge | | | Feed 1 | Feed 2 | | | Feed 3 | |
|---|---|---|---|---|---|---|---|---|---|
| Ex. No. | PE [g] (PE no.) | CTA [g] (CTA no.) | S [g] (S no.) | M [g] | FRI [g] (FRI no.) | PE [g] (PE no.) | S [g] (S no.) | CTA [g] | S [g] (S no.) |
| 1 | 230 (1) | — | 290 (2) | 540 (1) | 5.11 (2) | 10 (1) | 65 (2) | 10.8 (2) + 29.5 (3) | 19.8 (2) |
| 2 | 123 (2) | — | 95 (2) | 253 (1) | 2.40 (2) | 5 (2) | 95 (2) | 51 (1) | — |
| 3 | 123 (5) | 45 (1) | 95 (2) | 253 (1) | 2.40 (2) | 5 (5) | 95 (2) | 12 (1) | — |
| 4 | 123 (5) | 43 (1) | 95 (1) | 253 (1) | 2.40 (2) | 5 (5) | 95 (1) | 14 (1) | — |
| 5 | 123 (5) | 45 (1) | 95 (1) | 253 (1) | 2.40 (2) | 5 (5) | 95 (1) | 12 (1) | — |
| 6 | 123 (2) | 51 (1) | 95 (1) | 253 (1) | 5.93 (1) | 5 (2) | 95 (1) | 6 (1) | — |
| 7 | 123 (7) | 28 (1) | 80 (2) | 285 (1) | 6.68 (1) | 5 (8) | 77 (2) | 29 (1) | — |
| 8 | 230 (5) | — | 290 (2) | 540 (1) | 5.11 (2) | 10 (5) | 65 (2) | 10.8 (2) + 29.5 (3) | 19.8 (2) |
| 9 | 230 (5) | — | 310 (2) | 420 (1) | 3.98 (2) | 10 (5) | 146 (2) | 8.4 (2) + 22.9 (3) | 48.7 (2) |
| 10 | 250 (3) | — | 247 (3) | 500 (1) | 3.55 (3) | — | 46 (3) | 10.0 (2) + 27.3 (3) | 27.7 (3) |
| 11 | 170 (5) + 60 (6) | — | 320 (2) | 480 (1) | 4.54 (2) | 10 (5) | 75 (2) | 9.6 (2) + 26.2 (3) | 44.2 (2) |
| 12 | 230 (4) | — | 340 (2) | 480 (1) | 4.54 (2) | 10 (4) | 65 (2) | 9.6 (2) + 26.2 (3) | 34.2 (2) |
| 13 | 170 (4) + 60 (6) | — | 341 (2) | 480 (1) | 4.54 (2) | 10 (4) | 64 (2) | 9.6 (2) + 26.2 (3) | 34.2 (2) |

TABLE 2

| Ex. No. | $T_L$ at 500 nm | Consistency at 25° C. | Mw (g/mol) |
|---|---|---|---|
| 1 | n.d. | solid | 4700 |
| 2 | n.d. | solid | 1700 |
| 3 | 99.3% | solid | 6000 |
| 4 | 98.3% | solid | 2200 |
| 5 | 97.9% | solid | 7100 |
| 6 | 97.4% | free-flowing | 9500 |
| 7 | n.d. | solid | 4300 |
| 8 | 98.7% | solid | 4200 |
| 9 | 99.7% | free-flowing | 4200 |
| 10 | 99.1% | free-flowing | 5800 |

TABLE 2-continued

| Ex. No. | $T_L$ at 500 nm | Consistency at 25° C. | Mw (g/mol) |
|---------|-----------------|------------------------|------------|
| 11      | 99.0%           | solid                  | 4200       |
| 12      | 99.6%           | free-flowing           | 4500       |
| 13      | 99.7%           | free-flowing           | 6900       |

III) Determination of Physical Properties

III.a) Viscoelastic Parameters
Viscosity as a Function of Temperature:

The viscosity profile as a function of temperature for the samples to be examined was examined by means of a rotary rheometer (DHR-1 from TA Instruments with Peltier system, plate/plate geometry, Ø 40 mm, h=1 mm) at temperatures of 20° C. to 80° C. Temperature ramp ($\gamma$=1% with $M_{min}$=100 µNm). Measurement temperature(s) of 80° C. to 20° C. and back, two runs each (cooling/heating rate 2 K/min). Measurement time 30 min per run.

To study the viscoelastic characteristics of the inventive polymer compositions, the viscosity profiles of the polymer compositions from preparation example 8 were determined as a function of temperature. The results are shown in FIGS. 1 to 4. As is apparent from the diagrams, the viscosity profile (FIG. 1) does not coincide in the upward and downward curves, which is attributable to the difference between the set and actual temperature of the sample. Two runs (run 1 and run 2) were conducted both for the downward measurement (80° C. to 20° C.) and for the upward measurement (20° C. to 80° C.). It was found here that the sample was unchanged.

The plot of the storage modulus was superimposed in FIG. 2, and the plot of the loss modulus in FIG. 3. In general, a transition worthy of closer inspection is observed in the range from 35° C. to 45° C., which is manifested especially in the maximum of the phase angle δ shown in FIG. 4.

Examples of Dishwashing Formulations
Total weight: 10 to 25 g

| Amount | Phosphate-free formulations Amount [% by wt.] | Phosphate-based formulations Amount [% by wt.] |
|--------|-----------------------------------------------|------------------------------------------------|
| Protease | 1-4 | 1-4 |
| Amylase | 0.2-3 | 0.2-3 |
| Polymer composition (no. 1-33) | 2-30 | 2-30 |
| Sodium percarbonate | 5-14 | 5-14 |
| TAED (100%) | 2-8 | 2-8 |
| Sodium disilicate | 1-8 | 1-8 |
| Sodium carbonate | 5-40 | 5-40 |
| Sodium citrate dihydrate | 0-45 | 1-10 |
| MGDA | 0-45 | 0-20 |
| Tripolyphosphate | 0 | 10-60 |
| Polyvinyl alcohol (film) | 0-15 | 0-15 |
| HEDP | 0.5-15 | 0.5-1.5 |
| Further ingredients (e.g. perfume, corrosion inhibitors, tableting aids, dyes, further auxiliaries) | | |
| Total | 100 | 100 |

The polymer composition may be incorporated into the formulation or may be present in the overall formulation in a separate region as a clear gel component separately from the other components (for example divided by polyvinyl alcohol film).

The invention claimed is:

1. A machine dishwashing formulation which comprises a polymer composition in gel form, obtainable by a process in which
   a) Providing a monomer composition M) consisting of
      A) at least one α,β-ethylenically unsaturated acid, and
      B) 0% to 0.1% by weight, based on the total weight of the monomer composition M), of crosslinking monomers having two or more than two polymerizable α,β-ethylenically unsaturated double bonds per molecule,
   b) Subjecting the monomer composition M) provided in step a) to a free-radical polymerization in the presence of at least one polyether component PE) selected from polyetherols having a number-average molecular weight of at least 200 g/mol and the mono- and di-($C_1$-$C_6$-alkyl ethers) thereof, surfactants containing polyether groups and mixtures thereof.

2. The formulation according to claim 1, with the proviso that, when the polyether component PE) comprises a polyetherol having repeat propylene oxide units or a mono- or di-($C_1$-$C_6$-alkyl ether) of a polyetherol having repeat propylene oxide units, the proportion of these repeat propylene oxide units averages not more than 18 units per molecule.

3. The formulation according to claim 1, wherein the free-radical polymerization in step b) is additionally effected in the presence of a solvent S) selected from water, $C_1$-$C_6$-alkanols, polyols other than PE), the mono- and dialkyl ethers thereof, and mixtures thereof.

4. The formulation according to claim 1, wherein the polymerization in step b) is effected in feed mode, by initially charging at least a portion of the polyether component PE) and optionally, if present, at least a portion of the solvent S), and supplying at least a portion of the monomer composition provided in step a) and at least one free-radical initiator FRI) to the initial charge.

5. The formulation according to claim 3, wherein the free-radical polymerization in step b) is additionally effected in the presence of a solvent S) and
   the reaction mixture at the start of the reaction in step b) comprises the solvent S) in an amount of 0.1% to 70% by weight, based on the total weight of the reaction mixture,
   the reaction mixture after conclusion of the reaction in step b) comprises the solvent S) in an amount 0.1% to 40% by weight, based on the total weight of the reaction mixture.

6. The formulation according to claim 3, wherein the free-radical polymerization in step b) is effected in the presence of a solvent S) selected from propylene glycol, dipropylene glycol, water and mixtures thereof.

7. The formulation according to claim 1, wherein the polymerization in step b) is effected at a temperature in the range from 20 to 150° C.

8. The formulation according to claim 1, wherein the monomer composition provided in step a) consist of acrylic acid A1) and optionally at least one further α,β-ethylenically unsaturated acid A2).

9. The formulation according to claim 8, wherein the further α,β-ethylenically unsaturated acid A2) is selected from carboxylic acids, sulfonic acids, phosphoric acids and mixtures thereof.

10. The formulation according to claim 8, wherein the further α,β-ethylenically unsaturated acid A2) is selected from methacrylic acid, ethacrylic acid, α-chloroacrylic acid, crotonic acid, maleic acid, itaconic acid, citraconic acid, mesaconic acid, glutaconic acid, aconitic acid, fumaric acid, 2-acrylamido-2-methylpropanesulfonic acid, vinylsulfonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, styrenesulfonic acid, vinylphosphonic acid, allylphosphonic acid and mixtures thereof.

11. The formulation according to claim 7, wherein the monomer composition M) consists exclusively of acrylic acid.

12. The formulation according to claim 1, wherein the free-radical polymerization is performed in the presence of a chain transfer agent.

13. The formulation according to claim 1, wherein the polyether component PE) comprises at least one polyetherol having a number-average molecular weight in the range from about 200 to 100 000 or a mono- or di-($C_1$-$C_2$-alkyl ether) thereof.

14. The formulation according to claim 1, wherein the polyether component PE) comprises or consists of at least one polyetherol or a mono- or di-($C_1$-$C_2$-alkyl ether) thereof comprising exclusively ethylene oxide units incorporated as alkylene oxide units.

15. The formulation according to claim 1, wherein the polyether component PE) comprises at least one surfactant containing polyether groups, selected from alkyl polyoxyalkylene ethers, aryl polyoxyalkylene ethers, alkylaryl polyoxyalkylene ethers, alkoxylated animal and/or vegetable fats and/or oils, fatty amine alkoxylates, fatty acid amide alkoxylates, fatty acid diethanolamide alkoxylates, polyoxyethylene sorbitan fatty acid esters, alkyl polyether sulfates, aryl polyether sulfates, alkylaryl polyether sulfates, alkyl polyether sulfonates, aryl polyether sulfonates, alkylaryl polyether sulfonates, alkyl polyether phosphates, aryl polyether phosphates, alkylaryl polyether phosphates, glyceryl ether sulfonates, glyceryl ether sulfates, monoglyceride (ether) sulfates, fatty acid amide ether sulfates, polyoxyalkylene sorbitan fatty acid esters and mixtures thereof.

16. The formulation according to claim 1, wherein the polyether component PE) comprises at least one surfactant containing polyether groups, selected from:

alkyl polyoxyalkylene ethers of the general formula (VI)

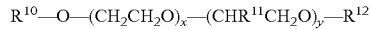

in which $R^{10}$ is a linear or branched alkyl radical having 8 to 22 carbon atoms, $R^{11}$ and $R^{12}$ are each independently hydrogen or a linear or branched alkyl radical having 1-10 carbon atoms or H, where $R^{12}$ is methyl, and x and y are each independently 0 to 300, where the sum of x and y is >0;

surfactants containing hydroxyl groups of the general formula (VII)

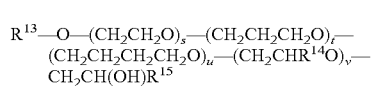

where
the sequence of the alkylene oxide units in the compounds of the formula (VII) is arbitrary, s, t, u and v are each independently an integer from 0 to 500, where the sum of s, t, u and v is >0, $R^{13}$ and $R^{15}$ are each independently a straight-chain or branched saturated $C_1$-$C_{40}$-alkyl radical or a mono- or polyunsaturated $C_2$-$C_{40}$-alkenyl radical, and $R^{14}$ is selected from methyl, ethyl, n-propyl, isopropyl and n-butyl; and fatty alcohol polyoxyalkylene esters of the general formula (VIII)

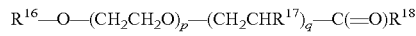

where
the sequence of the alkylene oxide units in the compounds of the formula (VIII) is arbitrary, p and q are each independently an integer from 0 to 500, where the sum of p and q is >0, $R^{16}$ and $R^{18}$ are each independently a straight-chain or branched saturated $C_1$-$C_{40}$-alkyl radical or a mono- or polyunsaturated $C_2$-$C_{40}$-alkenyl radical, and $R^{17}$ is selected from methyl, ethyl, n-propyl, isopropyl and n-butyl.

17. The formulation according to claim 1, wherein the polymer composition has a content of acid groups of 1.5 mmol/g to 15 mmol/g.

18. The formulation according to claim 1, wherein the polymer composition has a transparency, reported as the $T_L$ measured at 500 nm, of at least 85% based on the transparency of water.

19. The formulation according to claim 1, wherein up to 80 mol % of the acid groups, in the polymer composition are in neutralized form.

20. The formulation according to claim 1, wherein the acid groups in the polymer composition are not in neutralized form.

21. The formulation according to claim 1, wherein the polymers present in the polymer composition have a weight-average molecular weight of from 1000 to 70 000 daltons.

22. The formulation according to claim 1, wherein the polymer composition has a solubility in water at 40° C. and a pH of 8 of at least 5 g/l.

23. The formulation according to claim 1, wherein the crosslinkers B) are used in an amount of 0% to 0.05% by weight, based on the total weight of the monomer composition M).

24. The formulation according to claim 1, wherein the monomer composition M) does not comprise any crosslinking monomers B) which have two or more than two polymerizable α,β-ethylenically unsaturated double bonds per molecule.

25. The formulation according to claim 1, wherein the formulation for machine dishwashing comprises the following components:
a) at least one polymer composition as defined in claim 1,
b) at least one builder,
c) optionally at least one enzyme,
d) optionally at least one bleach,
e) water,
f) optionally at least one thickener, and
g) optionally at least one additive.

26. A method for machine cleaning of dishware, in which the dishware to be cleaned is contacted with a treatment solution comprising the formulation for machine dishwashing as defined in claim 25.

27. The formulation according to claim 25, wherein the at least one additive is selected from the following additives other than a): surfactants, bases, corrosion inhibitors, defoamers, dyes, fragrances, fillers, solubilizers and organic solvents.

28. The formulation according to claim 1, wherein the polymer formulation is in gel form for machine dishwashing formulations that are also in gel form.

29. The formulation according to claim 1, wherein the formulation further comprises a phosphate.

30. The formulation according to claim 1, wherein said α,β-ethylenically unsaturated acid is selected from the group consisting of methacrylic acid, ethacrylic acid, α-chloroacrylic acid, crotonic acid, maleic acid, itaconic acid, citraconic acid, mesaconic acid, glutaconic acid, aconitic acid, fumaric acid, 2-acrylamido-2-methylpropanesulfonic acid, vinylsulfonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, styrenesulfonic acid, vinylphosphonic acid, allylphosphonic acid and mixtures thereof.

31. The formulation according to claim 1, wherein the polymer composition in gel form, has none or only some of the acid groups of the polymer composition that are neutralized.

32. The formulation according to claim 1, wherein the polymer composition in gel form, has none of the acid groups of the polymer composition that is neutralized.

33. The formulation according to claim 1, wherein step b) is specified as follows:
b) the monomer composition M) provided in step a) is subjected to a free-radical polymerization in the presence of at least one polyether component PE) selected from
1) the mono- and di-($C_1$-$C_6$-alkyl ethers) of polyetherols having a number-average molecular weight of at least 200 g/mol
2) nonionic surfactants of the general formula (VI)

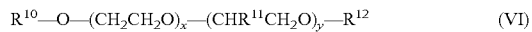

in which $R^{10}$ is a linear or branched alkyl radical having 6 to 22 carbon atoms,
$R^{11}$ and $R^{12}$ are each independently hydrogen or a linear or branched alkyl radical having 1 to 10 carbon atoms or H,
x=1 to 100 and y=0 to 30,
3) surfactants containing hydroxyl groups of the general formula (VII)

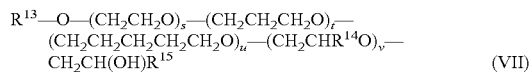

where
the sequence of the alkylene oxide units in the compounds of the formula (VII) is arbitrary,
s, t, u and v are each independently an integer from 0 to 500, where the sum of s, t, u and v is >0, $R^{13}$ and $R^{15}$ are each independently a straight-chain or branched saturated $C_1$-$C_{40}$-alkyl radical or a mono- or polyunsaturated $C_2$-$C_{40}$-alkenyl radical, and
$R^{14}$ is selected from methyl, ethyl, n-propyl, isopropyl and n-butyl, and
4) mixtures thereof.

34. A machine dishwashing formulation which comprises phosphate-free formulation comprising
1 to 4% by weight of protease,
0.2 to 3% by weight amylase,
2 to 30% by weight of a polymer composition in the gel form,
5 to 14% by weight of sodium percarbonate,
2 to 8% by weight of N,N,N',N'-tetraacylated amines,
1 to 8% by weight of sodium disilicate,
5 to 40% by weight of sodium carbonate,
0 to 45% by weight of Sodium citrate dihydrate,
0 to 45% by weight of L-glutaminediacetic acid, methylglycinediacetic acids and salts thereof,
0 to 15% by weight of polyvinyl alcohol,
0.5 to 8% by weight of phosphonic acids and
and optionally perfume, corrosion inhibitors, tableting aids or dyes and
wherein the formulation does not contain any phosphate and all weight percentages are based on the total weight of the formulation.

35. A machine dishwashing formulation which comprises formulation comprising
1 to 4% by weight of protease,
0.2 to 3% by weight amylase,
2 to 30% by weight of a polymer composition in the gel form,
5 to 14% by weight of sodium percarbonate,
2 to 8% by weight of N,N,N',N'-tetraacylated amines,
1 to 8% by weight of sodium disilicate,
5 to 40% by weight of sodium carbonate,
1 to 10% by weight of sodium citrate dihydrate,
0 to 20% by weight of L-glutaminediacetic acid, methylglycinediacetic acids and salts thereof,
10 to 60% by weight of alkali metal orthophosphates and/or polyphosphates
0 to 15% by weight of polyvinyl alcohol,
0.5 to 8% by weight of phosphonic acids and
optionally perfume, corrosion inhibitors, tableting aids or dyes and all weight percentages are based on the total weight of the formulation.

36. The formulation according to claim 1, wherein the polymer is the form of a transparent gel.

* * * * *